United States Patent
Fu et al.

(10) Patent No.: US 7,715,673 B2
(45) Date of Patent: May 11, 2010

(54) IMAGING SYSTEM

(75) Inventors: Ling Fu, Wuhan (CN); Min Gu, Doncaster (AU); Xiaosong Gan, Pascoe Vale (AU)

(73) Assignee: Swinburne University of Technology, Hawthorn VIC (AU)

( * ) Notice: Subject to any disclaimer, the term of this patent is extended or adjusted under 35 U.S.C. 154(b) by 0 days.

(21) Appl. No.: 11/917,553

(22) PCT Filed: Jun. 16, 2006

(86) PCT No.: PCT/AU2006/000842

§ 371 (c)(1),
(2), (4) Date: Feb. 11, 2008

(87) PCT Pub. No.: WO2006/133509

PCT Pub. Date: Dec. 21, 2006

(65) Prior Publication Data
US 2008/0205833 A1 Aug. 28, 2008

(30) Foreign Application Priority Data
Jun. 16, 2005 (AU) .............. 2005903158
Oct. 17, 2005 (AU) .............. 2005905741

(51) Int. Cl.
*G02B 6/02* (2006.01)

(52) U.S. Cl. ............ 385/123; 385/15; 385/31; 385/95; 385/96

(58) Field of Classification Search ............ 385/15, 385/31, 123, 95, 96, 97, 98, 99
See application file for complete search history.

(56) References Cited

U.S. PATENT DOCUMENTS 4,983,040 A  1/1991  Chu et al.
5,929,986 A  7/1999  Slater et al.

(Continued)

FOREIGN PATENT DOCUMENTS

EP  0498115  8/1992

(Continued)

OTHER PUBLICATIONS

M.T. Myaing, et al; "Enhanced two-photon biosensing with double-clad photonic crystal fibers;" Optics Letters, vol. 28, No. 14, Jul. 15, 2003.

(Continued)

*Primary Examiner*—Jennifer Doan
(74) *Attorney, Agent, or Firm*—Ladas & Parry LLP

(57) ABSTRACT

An imaging system including a multi-mode fiber and a gradient index (GRIN) lens. The invention also relates to a system including a multi-mode fiber, such as a double-clad photonic crystal fiber, for transmitting an excitation signal to a sample for the purpose of imaging, and a scanning mechanism, which preferably includes a microelectromechanical system (MEMS) mirror, for reflecting the excitation signal in varying directions in order to scan the sample.

17 Claims, 18 Drawing Sheets

U.S. PATENT DOCUMENTS

| | | |
|---|---|---|
| 5,973,779 A | 10/1999 | Ansari et al. |
| 6,038,363 A | 3/2000 | Slater et al. |
| 6,512,867 B2 * | 1/2003 | Brosnan .................. 385/27 |
| 6,816,513 B2 * | 11/2004 | Wang et al. ................. 372/6 |
| 2002/0131139 A1 | 9/2002 | Mandella et al. |
| 2002/0159055 A1 | 10/2002 | Bennett et al. |
| 2004/0161199 A1 | 8/2004 | Oh et al. |
| 2004/0245445 A1 | 12/2004 | Suzuki |
| 2004/0260148 A1 | 12/2004 | Schnitzer |
| 2005/0116038 A1 | 6/2005 | Lewis et al. |
| 2005/0143664 A1 | 6/2005 | Chen et al. |

FOREIGN PATENT DOCUMENTS

| | | |
|---|---|---|
| GB | 2338568 | 12/1999 |
| JP | 10137174 | 5/1998 |
| JP | 2002296018 | 10/2002 |
| JP | 2005257507 | 9/2005 |
| WO | WO2005/000110 | 1/2005 |
| WO | WO2005/091029 | 9/2005 |
| WO | WO2006/014392 | 2/2006 |
| WO | WO2006/045936 | 5/2006 |

OTHER PUBLICATIONS

Ling Fu, et al; "Nonlinear optical endoscopy based on a double-clad photonic crystal fiber and a MEMS mirror" Optics Express Feb. 6, 2006/ vol. 14, No. 3, pp. 1027-1032.

Damian Bird, et al; "Compact two-photon fluorescence microscope based on a single-mode fiber coupler" Optics Letters Jun. 15, 2002 / vol. 27, No. 12, pp. 1031-1033.

Ling Fu, et al; "Use of a single-mode fiber coupler for second-harmonic-generation microscopy" Optics Letters Feb. 15, 2005/ vol. 30, No. 4, pp. 385-387.

Ling Fu, et al; "Nonlinear optical microscopy based on double-clad photonic crystal fibers" Optics Express, Jul. 11, 2005/ vol. 13, No. 14, pp. 5528-5534.

* cited by examiner

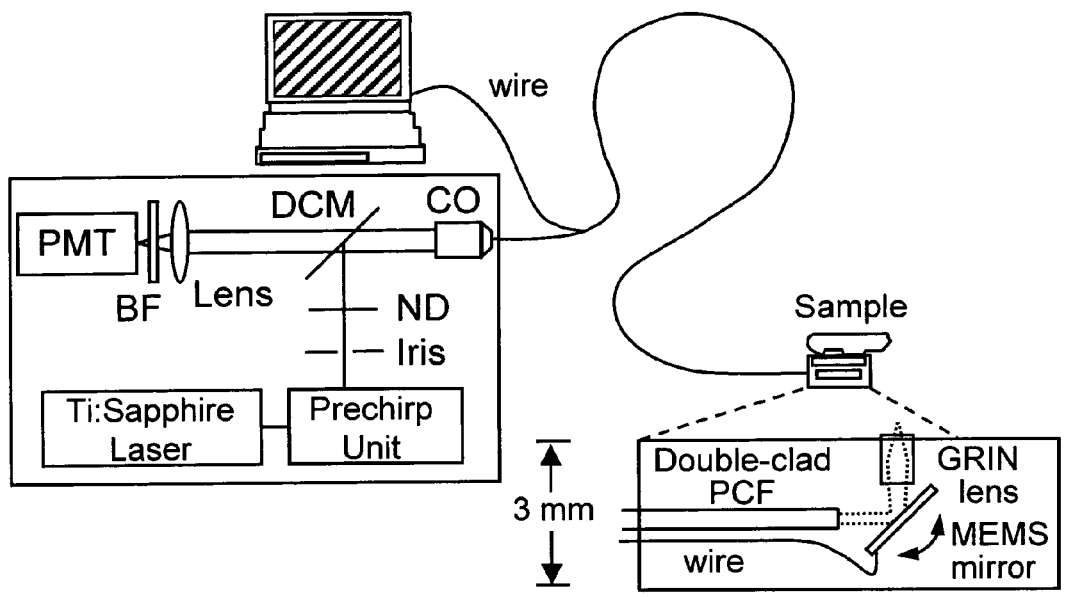
Figure 14a
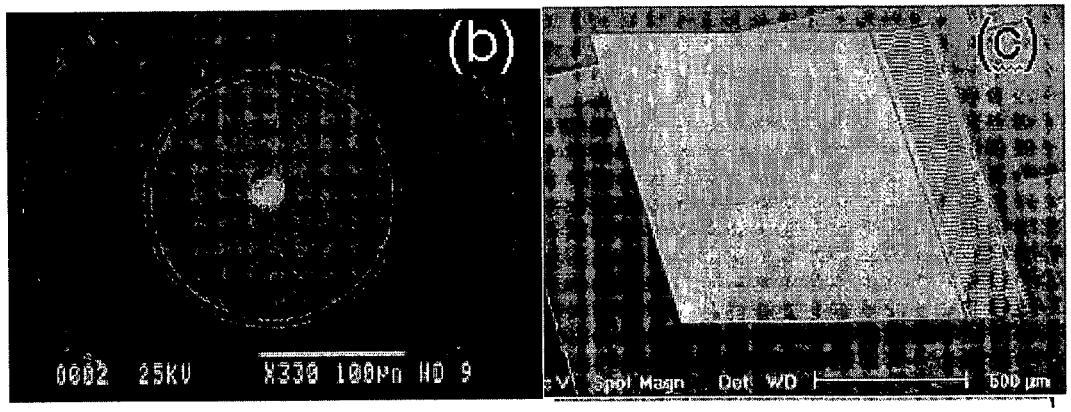
Figure 14b
Figure 14c

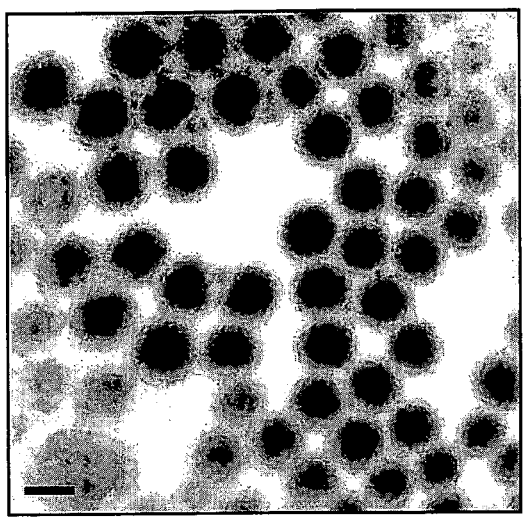 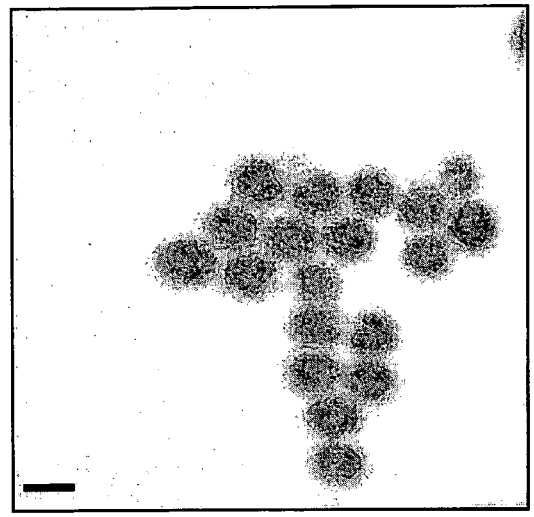
Figure 23a　　　　　Figure 23b
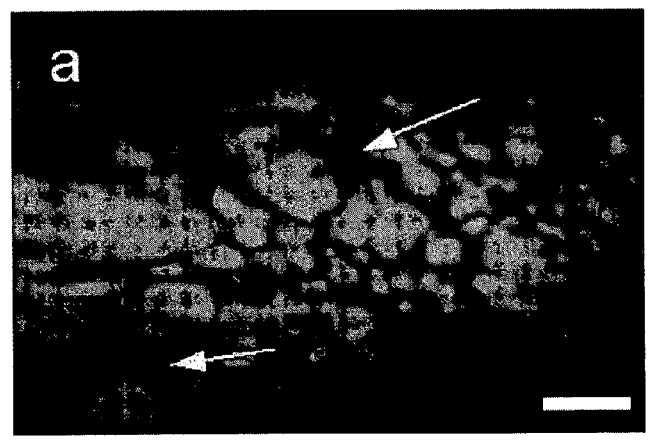
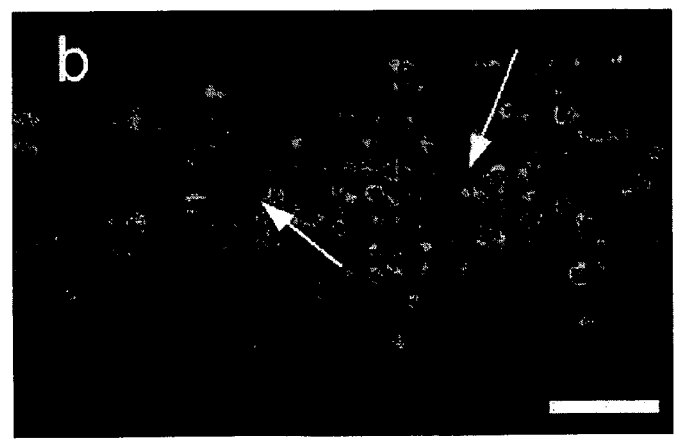
Figure 24

IMAGING SYSTEM

RELATED APPLICATIONS

This application claims priority from Australian Provisional Application AU 2005903158 and AU 2005905741, the contents of which are incorporated herein by reference.

FIELD OF THE INVENTION

This invention relates to the field of imaging using optic fibers particularly, but not exclusively, for use in microscopy and endoscopy.

BACKGROUND OF THE INVENTION

It is known to use a single-mode fiber in a two-photon fluorescence endoscope. The fiber has a core with a small numerical aperture (NA), which acts as both the source and detection aperture. Transmission characteristics of the single-mode fiber allow for relatively high excitation efficiencies and resolution to be achieved but low collection efficiency results.

Multi-mode fibers, such as double-clad photonic crystal fibers (DCPCFs) have recently been used for imaging. Such fibers have a single-mode inner core, with a small NA to provide a high efficiency excitation signal. A larger NA multi-mode layer surrounds the core, within an outer cladding, to provide high collection efficiency, although somewhat reduced resolution as compared to the single-mode fiber.

The advantages of DCPCFs have been demonstrated for optical imaging in endoscopy, as disclosed in an article D. Yelin, et al, "Double-clad fiber for endoscopy", Optics Letters, Vol. 29, No. 20, 2408 (2004). Further, improved detection efficiency has been investigated in relation to two-photon fluorescence detection, as disclosed in M. Myaing, et al, "Enhanced two-photon biosensing with double-clad photonic crystal fibers", Optics Letters, Vol. 28, No. 14, 1224 (2003).

OBJECT OF THE INVENTION

The present invention seeks to provide an improved imaging system and method.

SUMMARY OF THE INVENTION

In accordance with the invention, there is provided an imaging system including a multi-mode fiber and a gradient index (GRIN) lens.

Preferably, the system forms part of an endoscope.

Preferably, the GRIN lens is positioned in spaced relation relative to an end of the fiber.

Preferably, the lens has a pitch of between 0.2 and 0.29 and is spaced from the fiber by a distance of between 0.5 and 10 mm.

In a further aspect, there is provided a system including a multi-mode fibre, such as a double-clad photonic crystal fibre, for transmitting an excitation signal to a sample for the purpose of imaging, and a scanning mechanism, which preferably includes a microelectromechanical system (MEMS) mirror, for reflecting the excitation signal in varying directions in order to scan the sample. Most preferably, the system is for non-linear endoscopy.

Preferably, the system includes a GRIN lens, positioned between the scanning mechanism and the sample.

In another aspect, there is provided a method including transmitting an excitation signal through the above-described system and varying the direction of the signal using a scanning mechanism, which is preferably in the form of a MEMS mirror, in order to scan a sample.

Preferably, the method is for non-linear endoscopy.

In another aspect, there is provided a system including a fibre, for transmitting an excitation signal to a sample for the purpose of imaging, and compensation means for compensating temporal broadening of the signal resulting from group-velocity dispersion introduced into the signal by the fibre.

Preferably, the compensation means includes a grating structure such as a grating pair or Bragg grating.

Preferably, the compensation means provides a prechirping function.

Preferably, the system is an endoscopic system which is preferably adapted for non-linear endoscopy.

Preferably, the system has a scanning mechanism which preferably includes a MEMS mirror for reflecting the excitation signal in varying directions in order to scan the sample.

Preferably, the fibre is double-clad photonic crystal fibre.

In another aspect, there is provided a method of imaging including compensating temporal broadening of an excitation signal passing through the above-described system.

Preferably, the compensating includes introducing negative group-velocity dispersion, preferably by way of a grating.

Preferably, the method is applied to an endoscopic system which is adapted for non-linear endoscopy.

Preferably, the method includes reflecting the signal in varying directions using a MEMS mirror, in order to scan a sample.

In yet another aspect, there is provided a photonic crystal fiber coupler for use in the above system and/or method.

In accordance with a related aspect, the splitting ratio in the photonic crystal fiber coupler is optimised to enhance detection efficiency of the imaging system. Preferably, fiber engineering is utilised to improve the performance of the fiber and fiber-optic system.

BRIEF DESCRIPTION OF THE DRAWINGS

The invention is described, by way of non-limiting example only, with reference to the drawings, in which:

FIG. 14(a) is a schematic diagram of the nonlinear optical endoscope. The endoscope probe is based on a double-clad PCF, a MEMS mirror, and a GRIN lens;

FIG. 14(b) is a far-field output pattern from a double-clad PCF at wavelength 800 nm overlaid on a SEM image;

FIG. 14(c) is a SEM image of the MEMS mirror;

FIG. 16(a) shows a series of SHG line profiles taken at a 10-µm step into rat tail tendon while

FIG. 23 shows negative two-photon fluorescence images obtained (a) through a double-clad PCF, a MEMS mirror and a GRIN lens, and (b) through a single-mode fibre coupler, a GRIN lens and a bulk scanning stage. The sample is fluorescent microsphere with a diameter of 10 µm. Scale bars present 10 µm;

FIG. 24 shows (a) In vitro imaging of rat large intestine tissue. Luminal epithelial tissues were stained with 1% acridine orange in Ringer's solution. Surface epithelial cells surrounding intestinal crypts (arrows) can clearly be seen. (b) in vitro imaging of rat stomach epithelial surface stained with 1% acridine orange in Ringers solution. Openings to the gastric pits of the stomach columnar mucosal tissue are clearly visible (arrows). Scale bars represent 20 µm.

DETAILED DESCRIPTION

Figure 1:
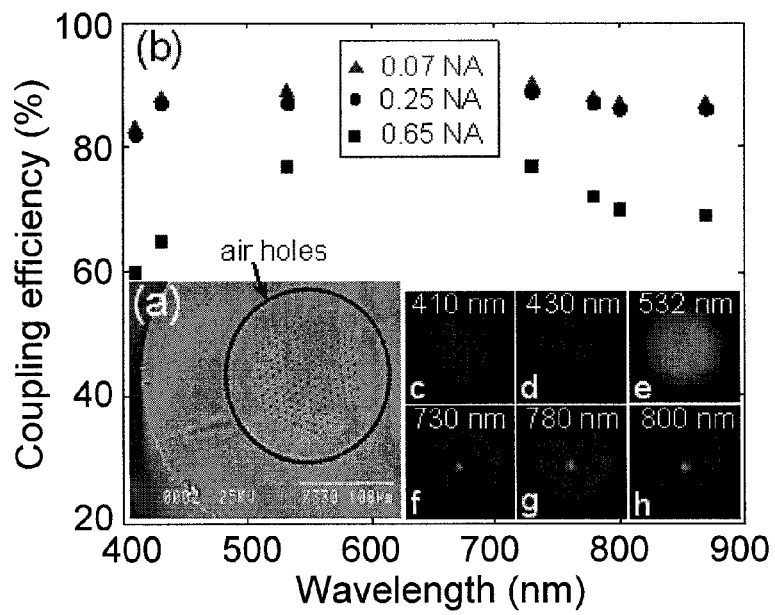
FIG. 1(a) is a scanning electron microscopy image of a double-clad PCF.
FIG. 1(b) illustrates coupling efficiency of the double-clad PCF in the wavelength range 410-870 nm for three values of the NA of coupling objectives (0.07, 0.25 and 0.65)
FIGS. 1(c)-(h) show digital camera photographs of an output pattern from a double-clad PCF between 410 and 800 nm. A microscope objective with NA 0.07 is used for coupling.
FIG. 1(i) is a schematic diagram of the nonlinear optical microscope based on a double-clad PCF.
Figure 1:
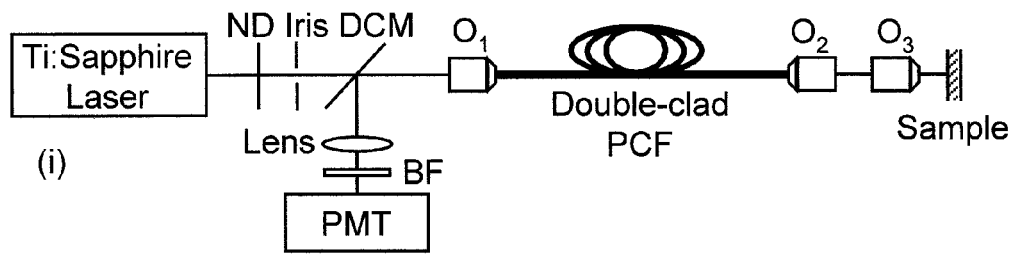

The invention will now be described with reference to use of a multi-mode fiber, firstly in relation to microscopy and secondly in relation to endoscopy, in combination with a GRIN lens and a MEMS mirror.

Nonlinear Optical Microscope Based on Double-Clad Photonic Crystal Fibers

1. Introduction

Nonlinear optical microscopy is based on the use of nonlinear optical effects such as two-photon absorption and second harmonic generation (SHG), which correspond to incoherent and coherent imaging processes, respectively[1,2]. These two imaging processes provide the cellular-level functionality and morphology information of a sample and exhibit advantages of an inherent sectioning ability, relatively deep optical penetration, and direct visualization of intrinsic indicators within biological tissue[1,2], A combination of two-photon excited fluorescence (TPEF) and SHG enables complementary information regarding functionalities and structures in tissue environment, which is crucial for tissue morphology and disease diagnostics[1,2]. To achieve compact and miniature nonlinear microscopes for in vivo applications, micro optics or flexible fiber-optic components such as optical fibers and optical fiber couplers are usually integrated into the imaging system to replace complicated bulk optics[3-9]. Although single-mode fibers (SMFs) can deliver a high quality laser beam and provide an enhanced sectioning capability due to the effective pinhole effect compared with multimode fibers or fiber bundles, the lower numerical aperture (NA) and the finite core size of the SMF give rise to a restricted sensitivity of a nonlinear optical microscope system. Therefore, a need exists for a high performance fiber-optic nonlinear optical microscope that can collect images efficiently and maintain the flexibility as well.

Recently, the emergence of photonic crystal fibers (PCFs) has been a renaissance of fundamental research and development on optical fibers. Double-clad PCFs originally developed for fiber lasers[10] have attracted research in the fields of biosensing and endoscopy for improvement in signal level due to its unique properties of the single-mode central core and the high NA multimode inner cladding[11,12]. However, the reported results[11,12] are not necessarily applicable in three-dimensional nonlinear optical microscopy for the following reasons. First, no imaging objective has been used[11,12] and thus the reported results do not hold for imaging a thick sample in which an optical sectioning property provided by an objective is necessary. Second, no measurement has been conducted for SHG which is a coherent signal rather than an incoherent signal such as TPEF. Their, due to the different NA of the central core and the inner cladding at different wavelengths, optimizing excitation delivery and emission collection with an objective for TPEF and SHG are different. Herein, we report on a TPEF and SHG microscope by the use of a double-clad PCF that can play a dual role of the efficient delivery of a near infrared illumination beam and the efficient collection of visible signals. The strength of both TPEF and SHG signals can be significantly improved for three-dimensional imaging with axial resolution of 2.8 µm and 2.5 µm. Our measurements show that the signal collection efficiency in a nonlinear optical microscope based on a double-clad PCF is approximately 40 times higher than that in a microscope based on a standard SMF.

2. Double-clad PCFs and Experimental Setup

The double-clad PCF we used (Crystal Fiber A/S) is shown in the inset (a) of FIG. 1, having a core diameter of 20 µm (i.e. a 17 µm mode field diameter at wavelength 780 nm), an inner cladding with a diameter of 165 µm and NA of 0.6 at wavelength 800 nm. The fiber core is surrounded by air holes with a hole to hole pitch ratio of 0.26. Within the outer cladding region of 340 µm in diameter, a ring of air holes is used to efficiently guide and collect light in the pure silica multimode inner cladding. The background propagation losses are as low as 10 dB/Km at wavelength 800 nm. As the double-clad PCF in the nonlinear microscope is used to deliver a near infrared excitation laser beam and collect nonlinear signals in the visible range, it is important to understand the properties of the fiber under various operating conditions. FIG. 1(b) shows the coupling efficiency of the fiber for three given values of the NA of the coupling objectives over the wavelength range between 410 and 870 nm. Moreover, the output light patterns of the fiber at different wavelengths are depicted in FIG. 1(c)-(h). The laser beams at various wavelengths are obtained in the same way as described elsewhere[8].

It is shown that the double-clad PCF offers the robust single-mode guidance of near infrared light in the central core and the efficient propagation of visible light within the multimode inner cladding. An efficiency of over 80% with a maximum of approximately 90% in the wavelength range of 410-800 nm is achievable, if the NA of coupling objectives is 0.07 or 0.25 to match the lower NA of the central core. However, there is a 20% degradation in the coupling efficiency by using the coupling objective with a NA of 0.65 due to the mode leakage in the inner cladding. It is found that approximate 28% of the output power from the double-clad fiber is guided in the central core at 800 nm when a coupling objective of NA 0.07 is used, whereas only 10% and 8% are in the core for a coupling objective of NA 0.25 and NA 0.65, respectively. Consequently, the use of a coupling objective with a NA of 0.07 can optimize the coupling efficiency at both the near infrared and the visible wavelength ranges. In particular, the coupling efficiency at wavelength 532 nm is approximately twice higher than that obtained with the single-mode fiber coupler[8]. In addition, it has been found from our experiment that the degree of polarization of the output laser beam in the central core is 0.84 at wavelength 800 nm, demonstrating that the linear polarization state is almost preserved in the central core. This conclusion together with FIG. 1 confirms the feasibility of a simultaneous improvement in TPEF and SHG imaging.

Based on above measurements the microscope imaging system as shown in FIG. 1(i) is constructed. A laser beam generated from a Ti:Sapphire laser (Spectra Physics, Mai Tai) with a repetition rate of 80 MHz and a pulse width of approximately 80 fs is coupled through an iris diaphragm and a microscope objective $O_1$ (0.65 NA, 40×) into the double-clad PCF with a length of approximately 1 meter. The size of the iris diaphragm is adjusted to achieve the maximum laser power guided in the central core. The output beam from the fiber is collimated by the objective $O_2$ of NA 0.07 before being launched into the imaging objective $O_3$ (0.85 NA, 40×). The coupling efficiency of the excitation laser beam to the double-clad PCF is approximately 88% in which case 38% of the power after the objective $O_2$ is delivered by the central core. The backward nonlinear signal via the PCF is collected by objective $O_1$ to match the high NA of the PCF inner cladding. The choice of a low NA objective $O_2$ and a high NA objective $O_1$ maximizes the collection efficiency of the nonlinear signals. A dichroic mirror (DCM) reflects the TPEF and SHG signals which are further filtered by a bandpass filter (BF) and focused onto a photomultiplier tube (PMT).

3. Axial Resolution and Signal Level

Figure 2:
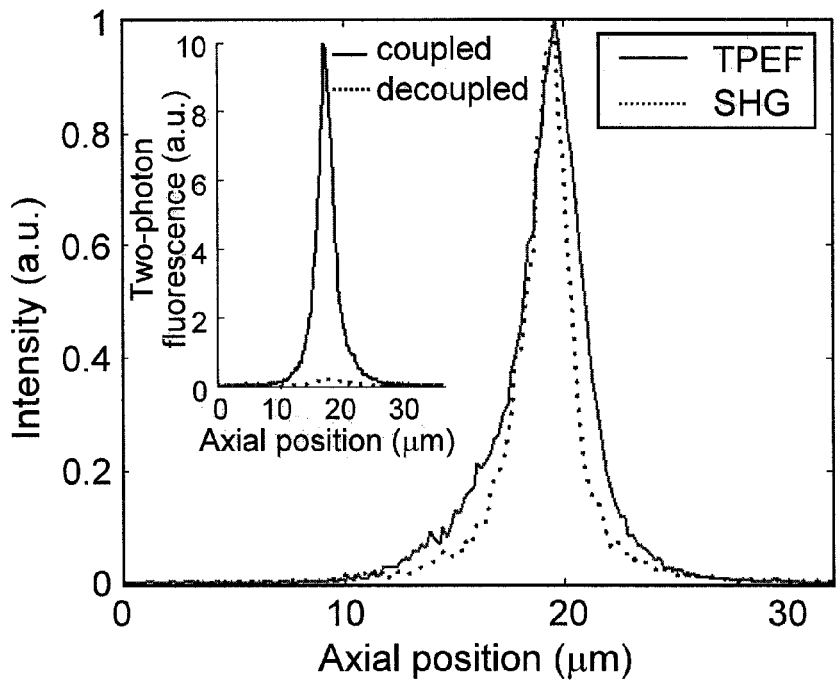
FIG. 2 represents axial responses of the TPEF and SHG signals from a thin layer of AF-50 dye at an excitation wavelength of 800 nm. Inset shows the axial responses for TPEF in the case of the well-coupled illumination in the central core and the decoupled illumination in the inner cladding of the fiber. The power on the sample is approximately 1.5 mW.

An experimental investigation into the axial resolution of the system for characterizing the three-dimensional imaging performance of the nonlinear microscope is executed by scanning a thin layer of AF 50 dye in the z direction[4,5]. The result is shown in FIG. 2, where the full width at half maximum (FWHM) of the axial responses of TPEF and SHG at an excitation wavelength of 800 nm is 2.8 µm and 2.5 µm, respectively, obtained by placing a 510/20 nm bandpass filter or a 400/9 nm bandpass filter before the PMT. It reveals a degradation of axial resolution of approximately 33% in the double-clad-PCF-based microscope, compared with that in a microscope which uses a single-mode-fiber-coupler[8]. This may result from the large area of the inner cladding, which effectively increases the pinhole size, and the centrally localized light distribution before the imaging objective (similar to FIG. 1h), which effectively decreases the NA of the imaging objective.

It should be pointed out that the laser beam from the inner cladding experiences a stronger effect of modal dispersion than that from the central core[13]. As a result, the laser beam delivered outside the central core contributes little to the nonlinear excitation. This feature is confirmed by the TPEF axial response depicted in the inset of FIG. 2, where the peak TPEF intensity when the excitation beam is well coupled in the central core is approximately 39 times as high as that when the excitation beam is decoupled transversely in the inner cladding.

Figure 3:
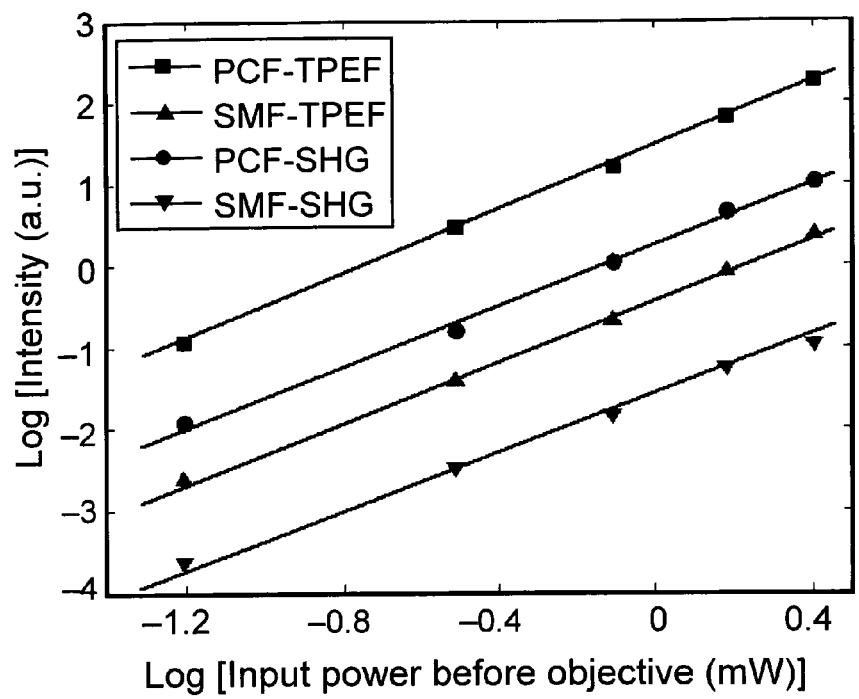
FIG. 3 shows detected intensity of TPEF and SHG from the double-clad-PCF-based and a standard SMF-based microscope as a function of the power before the imaging objective.

To investigate the signal level of the double-clad PCF-based nonlinear microscope, the strength of the axial responses of TPEF and SHG from the double-clad PCF was compared with a standard SMF (Newport, F-SBA). The fused-silica SMF has an operation wavelength of 820 nm, a core/cladding diameter ratio of approximately 4/125 and NA 0.16[6]. The coupling efficiency of the SMF of a 1-m length is approximately 30% at 800 nm[6]. The FWHM of the axial response with the two types of the fibers is kept the same for a given excitation power. The peak intensity of the axial responses from the two fibers as a function of the power before the imaging objective is shown in FIG. 3 on a log-log scale, where the slope of two demonstrates the quadratic dependence of the TPEF and SHG intensity on the excitation power. It is clearly observed that the detected intensity of the nonlinear signals from the double-clad PCF is approximately 6.8 times stronger than that from the SMF in the case of the same excitation power delivered to the sample. As a result, if one considers that the excitation beam in the central core of the two types of the fibers actually result in the nonlinear process, an enhancement of approximately 40 times in the nonlinear signal intensity detected through the double-clad PCF is achieved.

It should be emphasized that FIG. 3 is physically different from that reported elsewhere in which case no imaging objective was used and the imaging system can not be used for three-dimensional nonlinear optical imaging[12]. FIG. 3 is measured from the peak intensity of the axial responses and is thus applicable for imaging a thick sample when an optical sectioning property[1,2] is critical. FIG. 3 also reveals that the double-clad PCFs can support efficient propagation for the incoherent TPEF signal as well the coherent SHG signal.

To further confirm the enhancement of the three-dimensional imaging efficiency by using double-clad PCFs, SHG optical sections are collected from a scale of black tetra fish with the PCF-based microscope and the fiber-coupler-based microscope[8], which are shown in FIGS. 4(a) and (b), respectively. If a comparison is drawn between FIGS. 4(a) and (b) by considering the NA and magnitude of the temporal broadening in two cases, the signal level of the PCF-based microscope system is increased by a factor of approximately 65.

Figure 5:
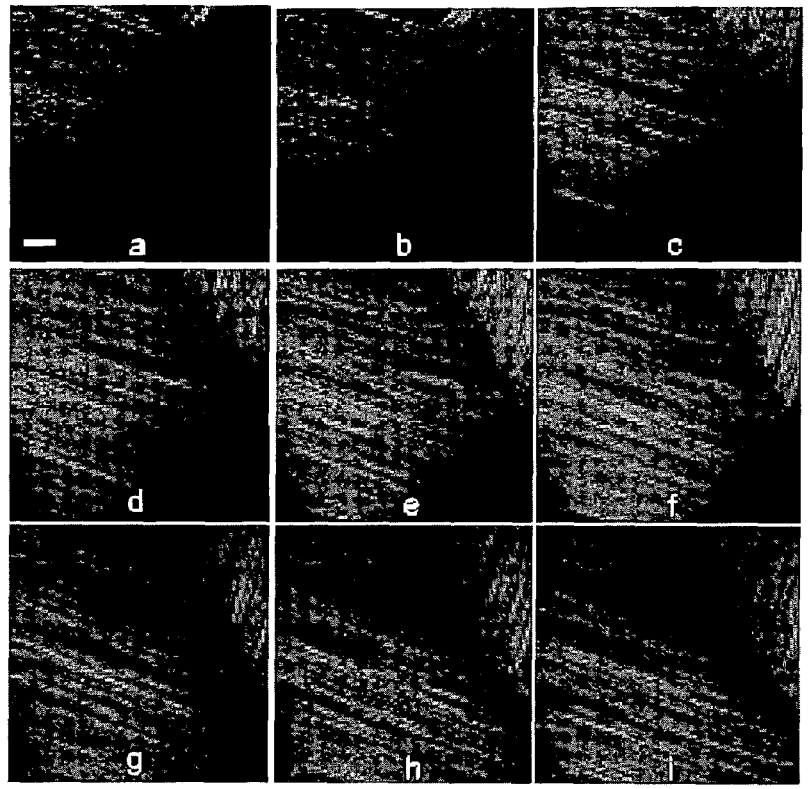
FIGS. 5(a)-(i) show a series of SHG image sections from the rat tail tendon in the nonlinear optical microscope using a double-clad PCF. The image section spacing is 2 µm and the excitation power through the fiber core is approximately 5 mW. The scale bar in (a) represents 10 µm.

FIG. 5 is a series of SHG images of rat tail tendon with 2-μm-depth steps, demonstrating the three-dimensional imaging capability of the nonlinear optical microscope based on the double-clad PCF through a thick tissue medium. The tendon is obtained from an 8-weeks old Sprague-Dawley rat tail, attached to the coverslip directly, and imaged within 2 hours of extraction. The image sections displayed in FIG. 5(a)-(i) clearly resolve the morphology of mature, well organized collage fibrils even at an imaging depth of 20 μm, showing the pronounced optical sectioning property of the system. The result implies that the efficient PCF-based nonlinear microscopy could be a potential tool for direct visualization of collagen-related diseases.

4. Conclusions

In conclusion, a nonlinear optical microscope has been presented, using a double-clad PCF. The new system exhibits a degree of polarisation of approximately 0.84 as well as a delivery efficiency of up to 90% in the near infrared wavelength region. Both the TPEF and SHG signal levels in the new system that has an optical sectioning property for three-dimensional imaging can be significantly improved by approximately 40 times in comparison with those in an SMF-based microscope. This feature is confirmed by nonlinear optical imaging of a scale of black tetra fish as well as by three-dimensional high resolution nonlinear optical imaging of rat tail tendon. Such a double-clad PCF-based microscopy system holds a promising future for application in nonlinear optical endoscopy.

Endoscopy and Characteristics of the GRIN Lens-Fiber Spacing Toward Applications in Two-Photon Fluorescence Endoscopy 1. Introduction Since its introduction, two-photon microscopy has been widely used as the best noninvasive means of fluorescence microscopy for three-dimensional imaging in thick tissue[14] and in live animals[15]. The advantages of two-photon microscopy over conventional microscopy stem primarily from the inherent optical sectioning effect, relatively deep optical penetration and flexible spectral accessibility[1,16]. More recently, two-photon imaging has been developed into the domain of endoscopy[3,7]. The emergence of two-photon fluorescence endoscopy could prove to be a useful diagnostic tool without the need for surgical biopsy both in basic research and in clinical pathology, which may produce spectra and images of tissue at the cellular level.

To achieve a compact and miniature microscope such as an endoscope, flexible fiber-optic components such as optical fibers, optical fiber couplers and gradient-index (GRIN) rod lenses may be integrated into the imaging system to replace complicated bulk optics[4,6,17]. A fiber-optic two-photon endoscope based on a single-mode optical fiber coupler, a GRIN rod lens, and a microprism has been constructed and exhibits an axial resolution of 3.2 μm[7].

A GRIN rod lens has a parabolic-shaped refractive index profile[18] which gives rise to unique optical properties compared with a normal microscope objective. The location of the focal point of a GRIN rod lens can be set by adjusting the magnitude of the gap between a source and the entrance face of the GRIN rod lens. Consequently, the numerical aperture (NA) of a GRIN rod lens is effectively changed as the gap between a source and a GRIN lens varies. Such an effective change in NA of a GRIN rod lens can affect the performance of fiber-optic two-photon fluorescence endoscopy[7] in three aspects. The first aspect is imaging resolution that depends on the square of the effective NA[19], the second one is the illumination and collection efficiency that shows a complicated dependence on the effective NA, and the third one is the two-photon fluorescence excitation strength that depends on the fourth power of the effective NA[6,4] although the total two-photon excitation signal generated is not a function of the excitation NA[4]. Therefore, a signal optimization of fiber-optic two-photon fluorescence endoscopy becomes possible and is thus necessary because two-photon fluorescence signal from biological tissues is usually weak.

Herein, we present an experimental investigation into the signal optimization of fiber-optic tow-photon fluorescence microscopy. The effect of the gap between a fiber end and a GRIN rod lens on the effective NA of the GRIN rod lens is studied. In particular, the dependence of the two-photon fluorescence intensity on the magnitude of the gap is revealed for three GRIN rod lenses of typical pitches lengths. The optimization performance is demonstrated by the three-dimensional images of fluorescence beads in a fiber-optic two-photon fluorescence microscope.

2. Experimental Setup

Figure 6:
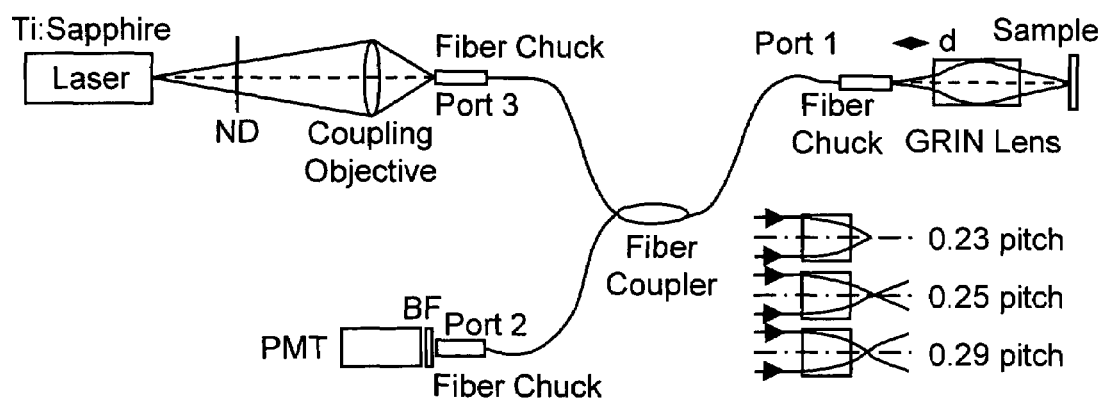
FIG. 6 is a schematic diagram of the fiber-optic two-photon fluorescence microscope based on a fiber coupler and a GRIN rod lens.

A schematic diagram of the fiber-optic two-photon fluorescence microscope based on a fiber coupler and a GRIN rod lens is depicted in FIG. 6. An ultrashort-pulsed laser beam at a wavelength of 800 nm and with a pulse width of 80 fs at a repetition rate of 80 MHz generated by a turnkey Ti:Sapphire laser (Spectra Physics, Mai Tai) is coupled through a microscope objective (Melles Griot, 20×/0.25 NA) into port 3 of the coupler. The fiber coupler used is a 50/50 three-port single-mode fiber coupler (Newport) designed for an operating wavelength of 785 nm. The coupler behaves as a low-pass filter in the visible wavelength range with a splitting ratio of between 99.6/0.4 and 99.7/0.3. The coupling efficiency from ports 3 to 1 is approximately 30% at wavelength 800 nm. The output beam from port 1 of the coupler crosses the gap and is focused by the GRIN rod lens. The fluorescence emitted from the sample is recollected by the GRIN rod lens and delivered via port 2 of the coupler into a photomultiplier tube masked with a 510±20 nm bandpass filter (BF). A neutral density filter wheel (ND) placed before the coupling objective allows the variation of the input power.

Three GRIN rod lenses of pitches 0.23, 0.25 and 0.29 to 830 nm (Newport) are chosen to confirm and compare the signal optimization condition in fiber-optic two-photon fluorescence microscopy. The difference of the pitch length implies that the focal position of the three GRIN rod lenses is at the surface of the lens, inside the lens and outside the lens, respectively, if a collimated beam is used (see FIG. 6). The 1.8-mm-diameter plano-plano GRIN lenses are designed for a wavelength of 830 nm. The 0.25-pitch GRIN lens has a NA of 0.6, while the NA of the 0.23-pitch and 0.29-pitch GRIN lenses is 0.46. The magnitude of the gap between the fiber coupler end and a GRIN lens, d, is controlled by a one-dimensional translation stage having a resolution of 10 µm. The maximum length of the gap is 5.5 mm to overfill the entrance face of the GRIN rod lens. The sample is a thin layer of AF-50 fluorescence dye, which has an average thickness of approximately 250 nm as measured by atomic-force microscopy[6]. The sample is driven by a scanning stage with a resolution of 0.1 µm and a 6 mm scanning range.

3. Determination of the Effective Numerical Aperture

Figure 7:
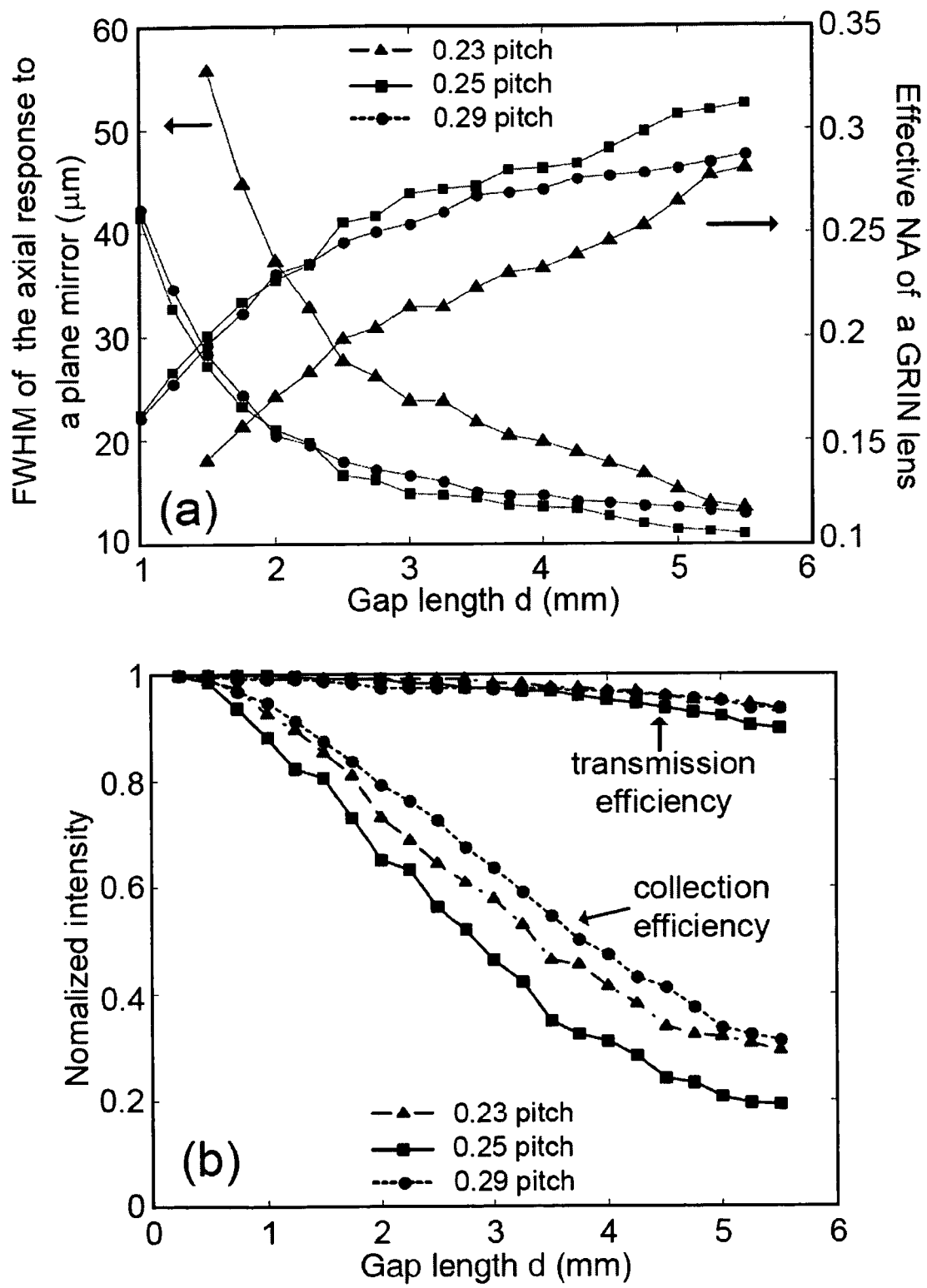
FIG. 7 illustrates a one photon reflection confocal axial response. (a) FWHM of the axial response to a plane mirror and effective NA of the GRIN rod lens as a function of gap d. (b) Transmission efficiency of the GRIN lens and peak intensity of the axial response to a plane mirror as a function of the gap d.

To achieve the effective NA of a GRIN rod lens, the axial response of the system to a plane mirror is recorded by continuous scanning in the z direction. Measurement of the full width at half maximum (FWHM) of the axial response curve allows for an analysis of the axial resolution of the system $\Delta z$, and then the effective NA of the GRIN rod lens, $\sin \alpha$ can be derived from $$u = (8\pi/\lambda) \Delta z \sin^2(\alpha/2), \quad (1)$$

where u is an axial optical coordinate and $\lambda$ is the wavelength of the illumination light[19,20]. Bu varying the gap length d, a set of axial response curves is obtained. The dependence of the FWHM of the axial response and the effective NA on the gap length for the three given GRIN rod lenses is depicted in FIG. 7(a). It is shown that the FWHM of the axial response drops rapidly to approximately 13.6 µm, 11 µm and 13 µm respectively, as the gap length increases. The decrease in the FWHM indicates the improvement in axial resolution and therefore the enhancement of the effective NA of the GRIN lens. The measured effective NA reflects on the system NA that combines the excitation and emission NA. As expected, for all the GRIN rod lenses, the effective NA increases gradually and tends towards a limit (approximately 0.29, 0.31, and 0.28 respectively) when the gap increases until the output laser beam from the fiber coupler overfills the entrance face of the GRIN rod lens.

In addition, analysis of the peak intensity of the axial responses reveals a decrease in coupling efficiency of the system approximately by 71%, 81% and 69%, respectively, as shown in FIG. 7(b). Such a signal reduction is caused by two physical processes. The first process is the coupling of illumination into a GRIN rod lens, which is confirmed by the transmitted power after the GRIN lens (FIG. 7(b)). In all cases, the transmission efficiency for the input power exhibits a slight degradation of approximately 6.3%, 10% and 6.3% respectively, as a result of increasing the gap length d in the range of between 0.25 mm and 5.5 mm. The second process is related to the mismatching between the fiber mode profile and the field distribution of the reflected signal on the end of the coupler. Once the fiber mode profile and the field distribution do not match each other, significant decrease of collection efficiency will occur. It should be pointed out that the experimental results of the coupling efficiency in FIG. 7(b) agree with the theoretical calculation of signal level in reflection-mode fiber-optic confocal scanning microscopy in the sense that the maximum reflected signal is achieved when the distance between the fiber and the GRIN lens is small[20].

4. Optimization of Two-Photon Fluorescence Signal

To study the two-photon fluorescence signal level in the fiber-optic two-photon microscope, a set of axial responses to the AF-50 fluorescence sheet is obtained. The FWHM of the axial response as a function of the gap length for the three GRIN rod lenses is plotted in FIG. 8(a), where the feature of the improvement in axial resolution is observed. It can be noted that the axial resolution of two-photon imaging is 15 µm, 11.6 µm and 13.3 µm for 0.23-pitch, 0.25-pitch and 0.29-pitch GRIN rod lenses, respectively, when the gap length is 5.5 mm.

Figure 8:
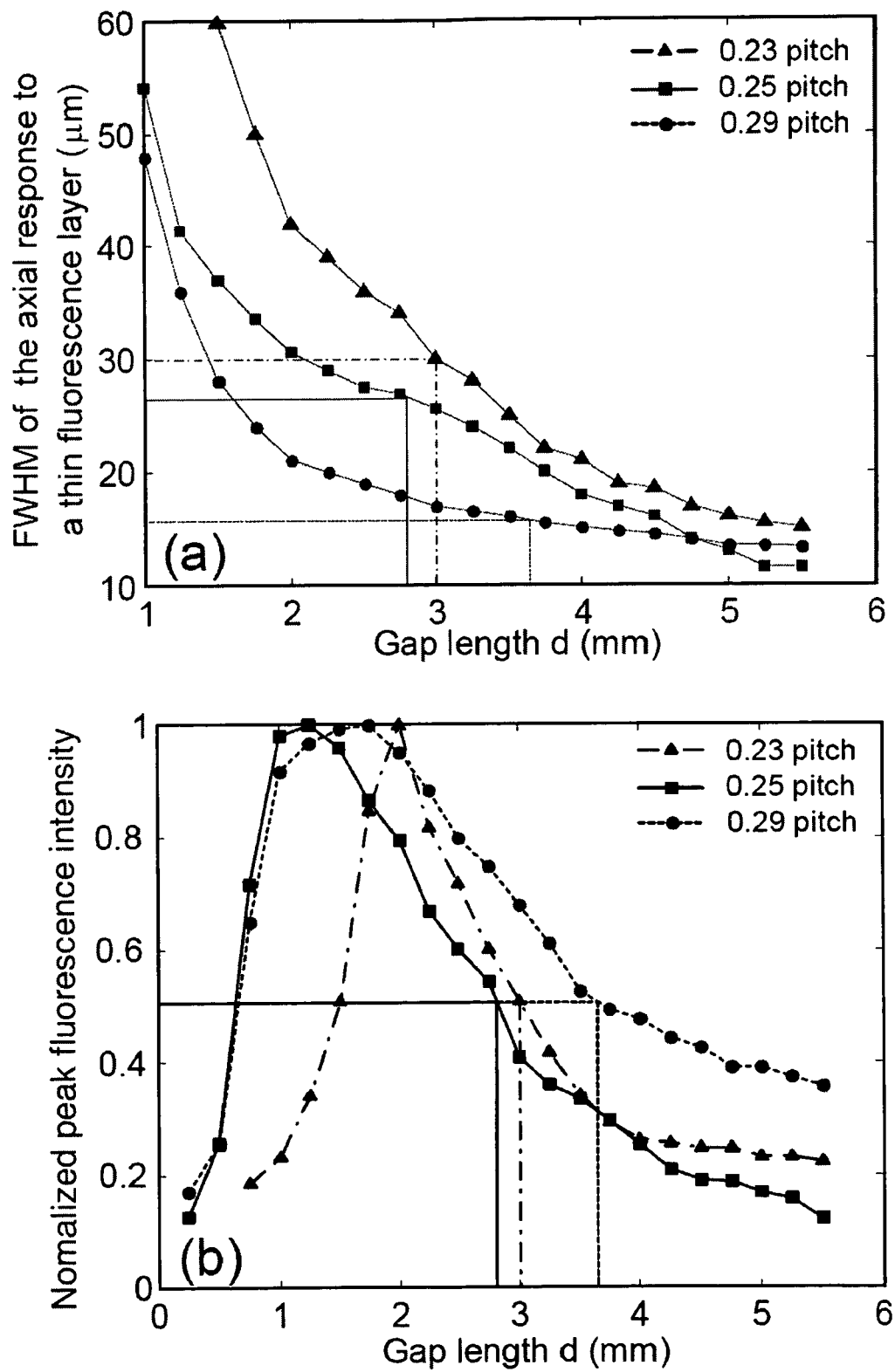
FIG. 8 shows a two-photon fluorescence axial response. (a) FWHM of the axial response to a fluorescence sheet as a function of the gap d. (b) Peak intensity of the axial response to a fluorescence sheet as a function of the gap d.

FIG. 8(b) shows the peak two-photon fluorescence intensity of the axial response as a function of gap lengths for the three GRIN lenses. It is clear that in all cases there exists the maximum fluorescence intensity collected by the fiber coupler over the gap range between 0.25 mm and 5.5 mm. Further observation from FIG. 8(b) reveals that the maximum fluorescence signal appears at a gap length of approximately 2 mm, 1.25 mm and 1.75 mm for the three GRIN lenses. The appearance of the maximum two-photon signal results from two competing physical processes. On the one hand, increasing the effective NA leads to the quick enhancement of the two-photon fluorescence signal because the two-photon excitation probability is proportional to the fourth power of the effective $NA^4$. On the other hand, as suggested in FIG. 7(b), the illumination and collection efficiency of the imaging system drops as the effective NA increases. Therefore, although the emitted two-photon fluorescence signal increases with the increase of the gap length, the two-photon fluorescence signal coupled backward by the fiber eventually reduces, as shown in FIG. 8(b).

The combination of FIGS. 8(a) and (b) implies that there is a trade-off between two-photon fluorescence axial resolution of the system and the two-photon fluorescence signal level that is related to the parameters of the GRIN lens and the optical wavelength. At the maximum signal level, the corresponding axial resolution is 42.0 µm, 38.5 µm and 24.0 µm, respectively, for 0.23-pitch, 0.25-pitch and 0.29-pitch GRIN rod lenses. Consider the gap length at which the two-photon fluorescence signal level drops to 50% of the maximum (FIG. 8(b)). The axial resolution corresponding to the three GRIN rod lenses is approximately 30.0 µm, 26.0 µm and 15.7 µm (FIG. 8(a)). Table 1 summarizes the effective NA, optimized axial resolution, and axial resolution at maximum fluorescence intensity etc, which would be considered in applications of two-photon fluorescence endoscopy.

TABLE 1

| RIN lens Pitch at 830 nm | Max. NA | Effective confocal NA | Optimized confocal Δz (μm) | Optimized TPF Δz (μm) | TPF Δz at half max. intensity (μm) | TPF Δz at max. intensity (μm) | d at max. intensity (mm) |
|---|---|---|---|---|---|---|---|
| 0.23 | 0.46 | 0.29 | 13.6 | 15 | 30 | 42 | 2 |
| 0.25 | 0.6 | 0.31 | 11 | 11.6* | 26 | 38.5* | 1.25 |
| 0.29 | 0.46 | 0.28 | 13 | 13.3 | 15.7 | 24 | 1.75 |

Figure 4:
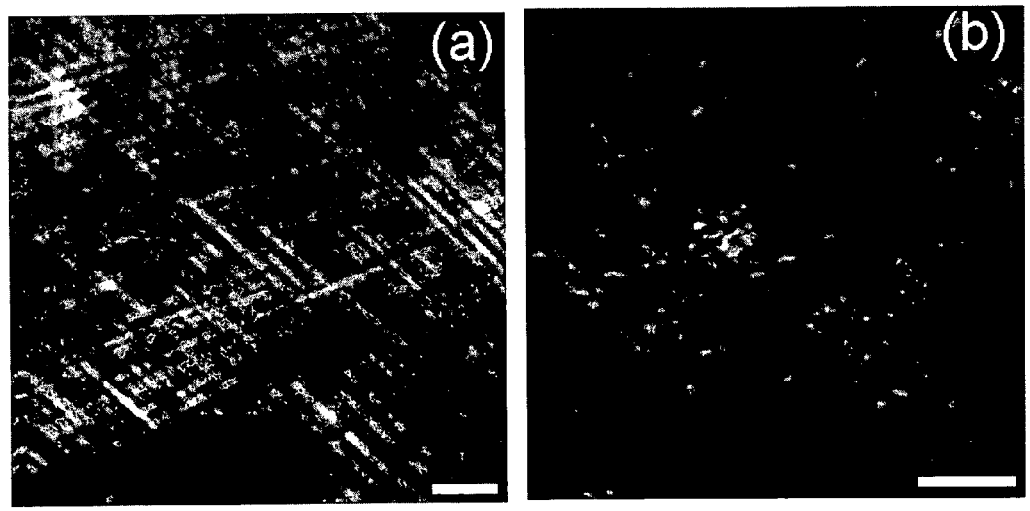
FIG. 4 shows a single optical section of SHG images from a scale of black tetra fish with (a) PCF-based microscope and (b) fiber-coupler-based microscope. Scale bars represent 20 µm.

*These axial resolution values are shown in FIG. 4 with 10 μm beads at ⅓ the axial focus spacing. Δz is axial resolution, and TPF represents two-photon fluorescence.

The appearance of the maximum signal level when the gap length increases can be understood from the optical transfer function analysis[21]. According to this method[19, 21], the signal level of a thin fluorescence sheet is proportional to the value of the two-dimensional in-focus optical transfer function $C_2(l)$ at $l=0$, where $l$ is the transverse spatial frequency of an object[19]. In the case of the fiber-optic two-photon fluorescence microscope that uses a single mode fibre coupler and a GRIN rod lens, the signal level can be expressed, if the input power from the Gaussian fibre profile and the power loss by the GRIN rod lens are considered, as $$\eta_2 = \frac{\beta A^4 C_2(l=0)}{1-\exp(-A)}, \quad (2)$$

where $\beta$ is a factor of normalization and $A=(2\pi a r_0/(\lambda d))^2$. Here $a$ and $r_0$ are the radius of the GRIN rod lens and the fiber mode profile, respectively, $\lambda$ is the illumination wavelength and $d$ is the gap length. It has been known from the previous study[21] that $C_2(l=0)$ decreases monotonically as A increases. As a result of the balance between $A^4/(1-\exp(-A))$ and $C_2(l=0)$, the signal level given by Eq. (2) leads to a maximum peak, qualitatively confirming the behaviour of FIG. 8(b).

Figure 9:
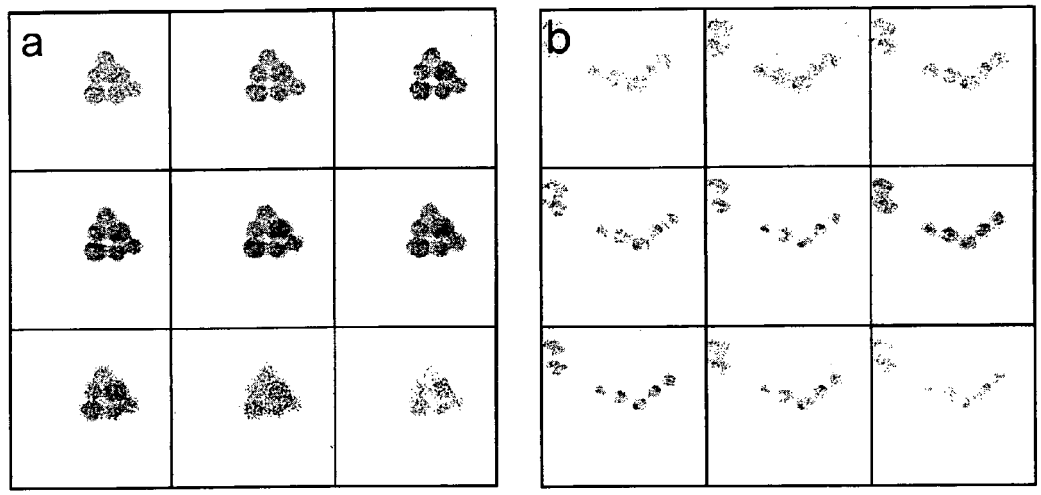
FIG. 9 is a series of negative x-y images of 10 µm fluorescence polymer microspheres acquired with a 0.25-pitch GRIN lens by (a) setting d=1.25 mm, with a slice spacing of 15 µm and (b) setting d=5.5 mm, with a slice spacing of 5 µm. Axial resolution for these two gap lengths are shown in Table 1. Each slice size is 100 µm×100 µm. Average power on the sample is 10 mW.

To show optimum imaging performance of the fiber-optic two-photon fluorescence microscope, two negative image sets of 10 μm fluorescence polymer microspheres shown in FIG. 9 are obtained with the 0.25-pitch GRIN rod lens when the gap between the fiber coupler end and the GRIN rod lens is 1.25 mm and 5.5 mm, respectively. The two image sets are recorded with the lateral size of 100 μm and the slice spacing of 15 μm and 5 μm, respectively. It is clearly observable that the two-photon fluorescence images have strong intensity but poor resolution with the gap where the optimization of the signal level is achieved (FIG. 9(a)). On the other hand, the optical sectioning ability of the system is optimized with poor signal level when the gap distance is maximum (FIG. 9(b)).

5. Conclusion

We have demonstrated that the fluorescence signal level and axial resolution is a function of the gap between the fiber coupler end and the GRIN rod lens for a fiber-optic two-photon fluorescence microscope. The collected two-photon fluorescence intensity exhibits a maximum value as the gap between the fiber coupler end and the GRIN rod lens enlarges, i.e. as the effective NA of a GRIN lens increases. The optimal two-photon fluorescence signal level appears at a gap length of approximately 2 mm, 1.25 mm and 1.75 mm for a GRIN rod lens of pitches 0.23, 0.25 and 0.29. The performance of the fiber-optic two-photon microscope is demonstrated by the three-dimensional images of fluorescence microspheres. These results elucidate choices in the signal to resolution trade-off in the application of fiber-optic two-photon fluorescence endoscopy to achieve visualization of biological tissues.

Imaging System with Multi-Mode Fiber and Grin Lens

The advantages associated with use of a GRIN lens may be further enhanced by combining such a lens with a multi-mode fiber, such as a DCPCF, to thereby realise improved image collection efficiencies.

Figure 10:
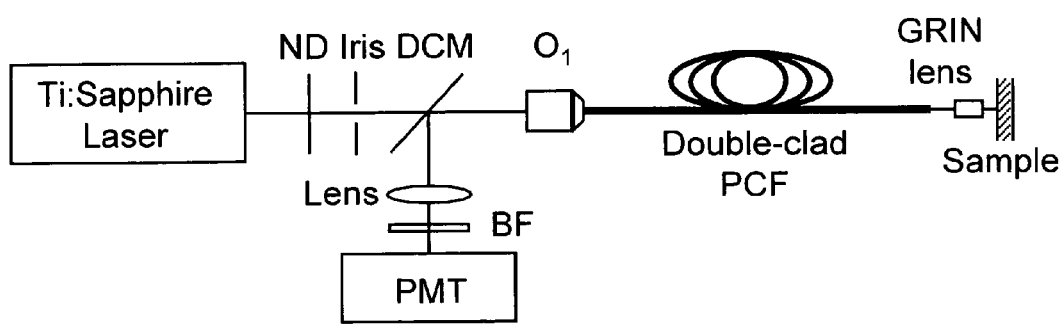
FIG. 10 is a schematic view of a nonlinear microscope using a double-clad PCF and GRIN lens.

An example of such a combination is shown in FIG. 10, where the lens forms part of a compact endoscope head of an imaging system used, for example, in nonlinear endoscopy for oesophagus imaging.

In that regard, the GRIN rod lens is adopted to replace the previous bulk microscope objective. The lens may be 0.5 mm in diameter and 0.2 pitch at 810 nm, for focussing the pulsed laser beam delivered by a multi-mode fiber in the form of a double-clad PCF onto the sample. The lens also serves to collect nonlinear signals at visible wavelength as well.

Figure 11:
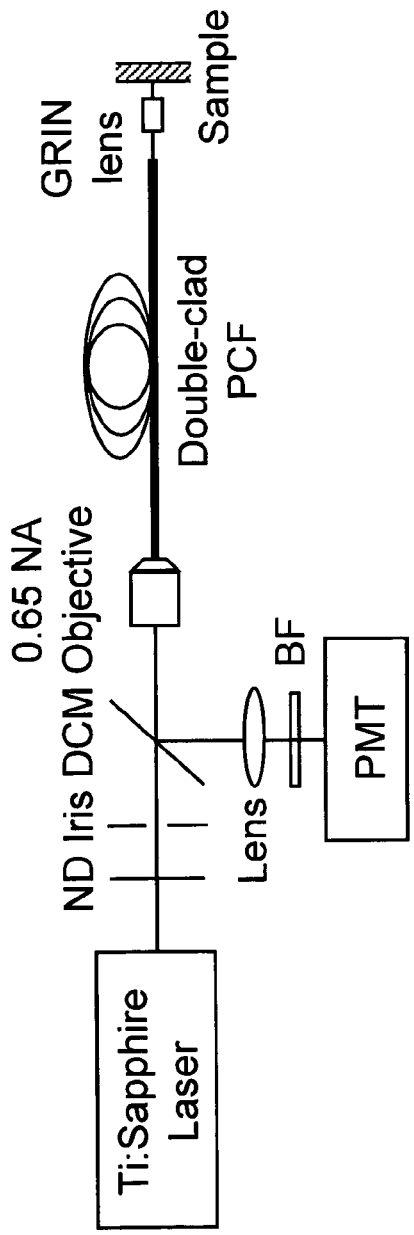
FIG. 11 illustrates an axial response of the microscope of FIG. 10.
Figure 12:
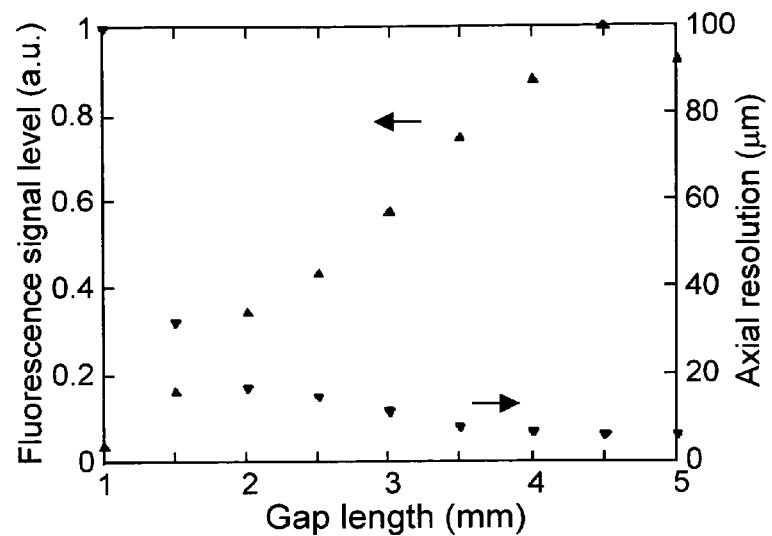
FIG. 12 illustrates a fluorescence signal level and axial resolution as a function of gap length.

As described above[22], the detected signal and the sectioning ability of the system have significant dependence on the gap length d. To optimize the collection efficiency of the system, a series of axial responses to the AF-50 fluorescence sheet are measured, as shown in FIG. 11, to derive the fluorescence signal level and axial resolution, which is depicted in FIG. 12. The optimized axial resolutions for TPEF and SHG are 6.2 μm and 5.4 μm respectively when the gap length is approximately 5 mm to fulfill the back aperture of the GRIN lens. It is also found that the detected two-photon fluorescence increases over the gap range from 1 to 4.5 mm. It might be due to high collection efficiency resulting from the large NA and detection aperture of the double-clad PCF.

Compared with the "trade-off" feature in the microscope using a single-mode fiber coupler and a GRIN lens[22], the use of double-clad PCFs is the ideal solution to achieve the optimization of the signal level and axial resolution simultaneously.

Figure 13:
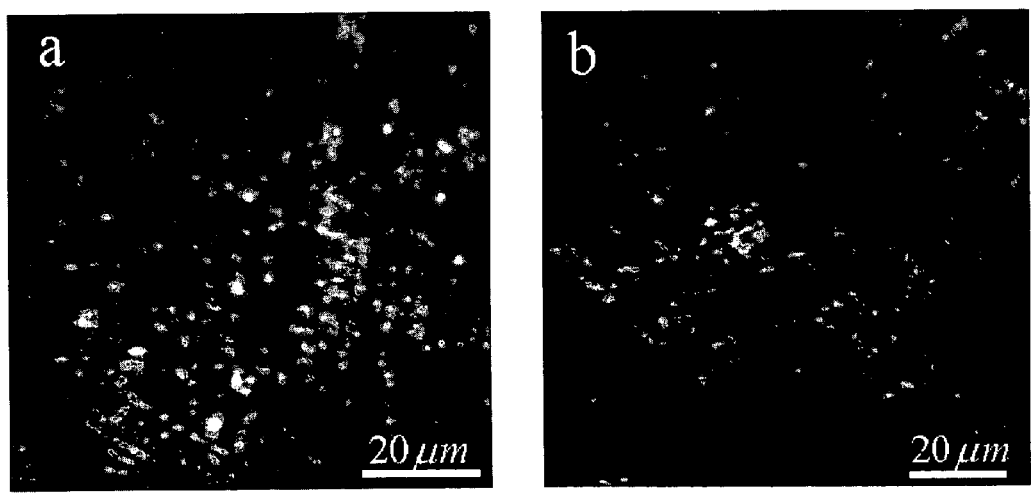
FIG. 13 shows a section of SHG image of fish scale in (a) PCF-GRIN based microscopy and (b) coupler-objective based microscopy.

FIG. 13 shows the a single section of SHG image of fish scale obtained by PCF-GRIN-based microscopy and coupler-objective-based microscopy. Signal level of the microscopy using a PCF and a GRIN lens is approximately 7.5 times as high as that in the coupler-objective-based microscopy. This result further confirms the enhancement of the signal collection from the double-clad PCF.

The three-dimensional imaging capability of the system has also been demonstrated by the oesophagus and the stomach imaging from an 8-week SD Rat. Nuclei of cells stained by AO were excited for two-photon fluorescence and connective tissue contributed to a second harmonic signal. The combination of the TPEF and SHG could provide the complementary information for cancer diagnosis at a sub-cellular level[23].

The nonlinear endoscope head can be further developed by the integration of a MEMS mirror[24] to achieve a scanning mechanism for scanning the sample, as described in more detail below.

Nonlinear Optical Endoscopy Based on a Double-Clad Photonic Crystal Fiber and a MEMS Mirror Two-photon fluorescence and second harmonic generation microscopy have enabled functional and morphological in vivo imaging. However, in vivo applications of those techniques to living animals are limited by bulk optics on a bench top. Fortunately, growing functionality of fiber-optic devices and scanning mirrors stimulate the race to develop nonlinear optical endoscopy. Here we report on a prototype of a non-linear optical endoscope based on a double-clad photonic crystal fiber to improve the detection efficiency and a MEMS mirror to steer the light at the fiber tip. The miniaturized fiber-optic nonlinear microscope is characterized by rat esophagus imaging. Line profiles from the rat tail tendon and esophagus prove the potential of the technology in application of surgical biopsy and early cancer detection.

Since its inception, multi-photon microscopy has emerged as one of the best non-invasive means of fluorescence microscopy[1]. Compared with its single-photon counterpart, two-photon fluorescence excitation offers an inherent optical sectioning property, a great penetration depth, and a flexible spectra accessibility for most fluorophores. Furthermore, accompanied nonlinear scattering processes such as second harmonic generation (SHG) from noncentrosymmetric structures, enables complementary information to visualize endogenous structures in tissues[2]. Although miniaturized microscopes have been achieved to perform nonlinear optical microscopy such as two-photon excited fluorescence (TPEF) and SHG imaging[7,8,25-35], three major obstacles make them difficult to be applicable within internal cavities of the body. The first one is the scanning mechanism which is adopted to form an image and maintain the flexibility and ultra-small size as well. Second, rigid probes based on combined gradient-index (GRIN) rod lenses can be inserted into deep tissues, but are not flexible to be incorporated into endoscopes to image internal organs. Finally, if a single-mode optical fiber or a fiber bundle is adopted to deliver a laser beam and collect signals, the low numerical aperture (NA) and the finite core size of the fibers give rise to a restricted sensitivity of the system. A possible way to overcome these obstacles is to guide excitation and emission beams using a length of fiber that exhibits two efficient transmission paths for excitation and emission wavelengths and to manipulate the optical beam by a micromirror with a diffraction-limited focus spot. Recent advances in photonic crystal fibers (PCFs)[31,32] and micro-electromechanical system (MEMS) technology[33] offer the possibility to achieve such a nonlinear optical endoscope allowing for high resolution imaging of internal organ systems. The previous study[32] demonstrates the detection efficiency of the double-clad PCF-based microscope is approximately 40 times higher than that in the single-mode-fiber-based microscope, mainly due to the large core size and high NA of the inner cladding. Here we report on a miniaturized nonlinear optical microscope based on a double-clad PCF and a MEMS scanning mirror. The endoscope-based line profiles from rat tail tendon and esophagus demonstrate the promising potential for developing a real-time nonlinear optical endoscope to enable early cancer detection at the cellular level.

Results

Endoscope Design

An ultra-small probe head is designed to fit the working channel of a flexible endoscope and connect to the bulk optical components via a flexible fiber, as shown in FIG. 14(a). The excitation laser beam coupled from the double-clad photonic crystal fiber[32] is reflected and scanned one-dimensionally by a MEMS mirror[33] with a maximum rotation angle of 17 degrees. A GRIN lens is used to focus the scanned laser beam at its back surface onto a sample. As a consequence, the endoscope head of the prototype system is approximately 3 mm in diameter, equipped with the MEMS mirror and the GRIN lens. The double-clad PCF we used (FIG. 14(b)) can play a dual role to offer the robust single-mode guidance of near-infrared light in the central core and the efficient propagation of visible light within the multimode inner cladding[32]. The MEMS mirror shown in FIG. 14(c) is 1 mm by 1 mm in size, coated with aluminium. It has a resonance frequency of 165 Hz, exceeding the scanning speed and angle requirements for most endoscopic applications[34].

Axial Resolution and Signal Level

Figure 15A:
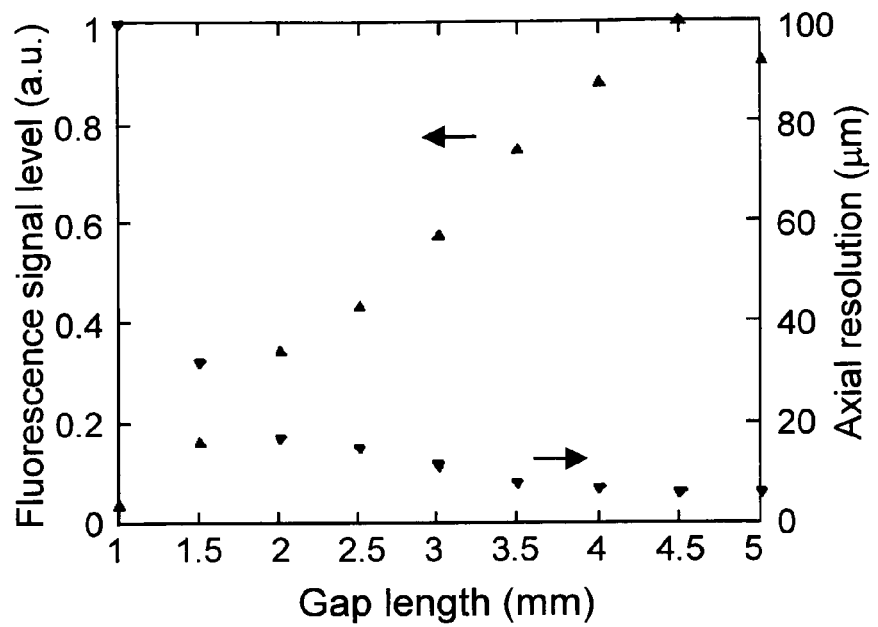
FIG. 15(a) illustrates optimization of signal level and axial resolution and FIG. 15(b) shows a Z projection of 8 slices through the rat oesophagus tissue stained with Acridine Orange. Two-photon fluorescence (red) and SHG (green) visualize cell nuclei and connective tissue, respectively. A GRIN lens used for imaging has a diameter of 0.5 mm and a NA of 0.5. Slice spacing is 5 µm. Scale bar represents 20 µm.

One of the advantages of nonlinear optical microscopy is its intrinsic optical sectioning ability in a thick sample. It should be pointed out that the axial resolution and the signal level of the system varies as a function of the gap length between the fiber and the back surface of the GRIN lens, as shown in FIG. 15(a). The optimized axial resolution of TPEF and SHG at an excitation wavelength of 800 nm for the system is approximately 6 μm and 5.4 μm, respectively. It is found that the optimized signal level of the endoscope is approximately 160 times higher than that of the single-mode-fiber-based two-photon fluorescence endoscope[23]. The enhancement of the signal level might result from the high NA and the large core diameter in the inner cladding of the double-clad PCF. The use of a prechirp unit consisting of a pair of gratings (FIG. 14(a)) can increase the signal level by one order of magnitude.

Tissue Imaging Using a GRIN Lens

Figure 15B:
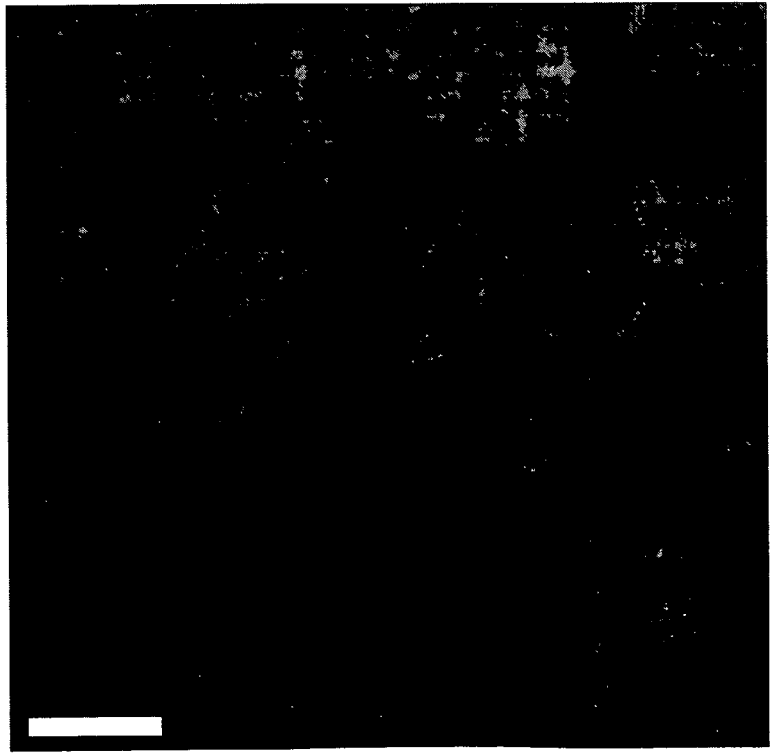

To prove the effectiveness of a single GRIN lens for endoscopy, the in vitro non-linear optical images from rat oesophagus are achieved using the double-clad PCF, the GRIN lens, and a 2-D scanning stage, as shown in FIG. 15(b). Only SHG signals from connective tissue can be observed to exhibit the morphology of the micro-structures. In rat oesophagus tissue, in vitro SHG signal originate from collagen is detectable using the double-clad PCF and the 0.2-pitch GRIN lens, demonstrating the potential of SHG in diagnosis of collagen-related diseases.

Endoscopic Imaging Using a MEMS Mirror

Figure 16A:
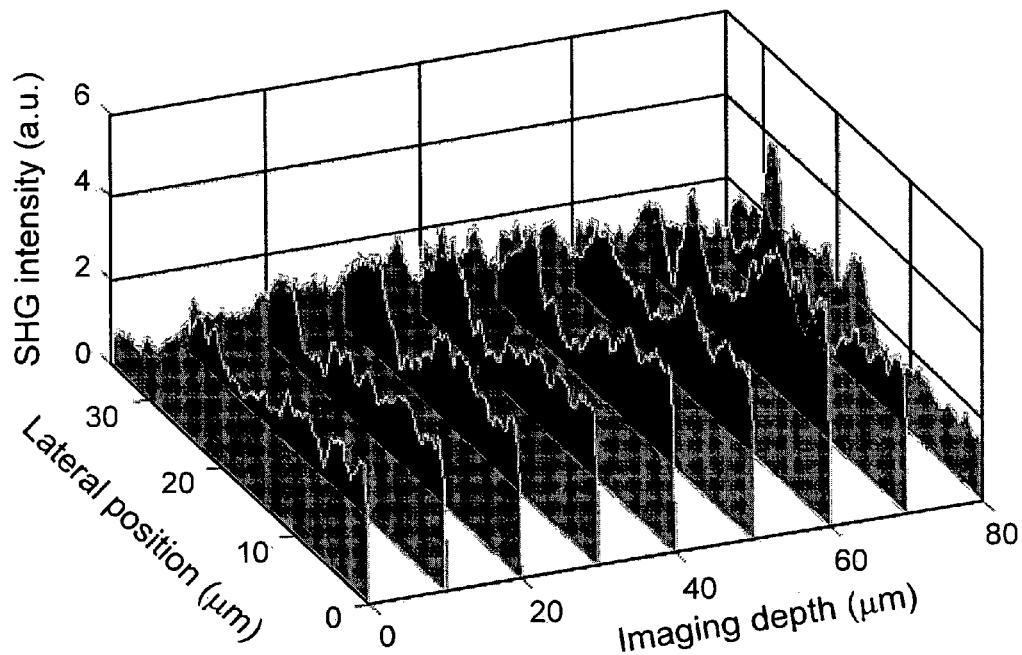
Figure 16B:
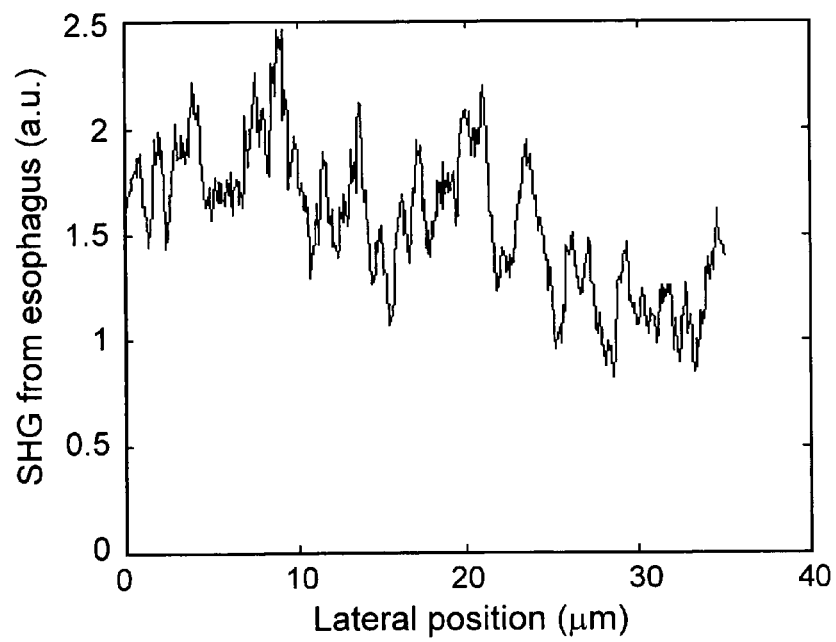
FIG. 16(b) illustrates a SHG line profile from unstained rat oesophagus tissue.

Rat tail tendon is used to characterise the non-linear optical endoscope which is comprised of the double-clad PCF, the GRIN lens, and the MEMS mirror. Rat tail tendon consists of abundance of Type I collagen fibrils, which could be modeled in wound healing, malignancy, and development. FIG. 16(a) illustrates a series of SHG line profiles from rat tail tendon with a depth spacing of 10 μm. In this case, a 0.2-pitch GRIN lens having a diameter of 1 mm is used and the field of view on the sample is approximately 35 μm which corresponds to an optical scanning angle of approximately 6 degrees of the MEMS mirror. In our experiments, as the laser beam is scanned at the back surface of the GRIN lens, the GRIN lens is underfilled and results in an axial resolution of approximately 10 μm. Further, a SHG line profile from the rat oesophagus tissue is shown in FIG. 16(b). The rat oesophagus is imaged directly after dissection without any staining and the excitation power on the sample resulting in SHG signals is approximately 30 mW. FIG. 16(b) confirms that the nonlinear optical endoscope probe based on the double-clad PCF, the GRIN lens and a MEMS mirror enables rat esophagus imaging in vitro.

Discussion

We have demonstrated experimentally the concept of nonlinear optical endoscopy based on a double-clad PCF, a GRIN lens and a MEMS mirror. A double-clad PCF has been used to deliver the pulsed excitation beam and collect non-linear optical signals with a detection efficiency enhanced by 160 times. Using a MEMS mirror as the scanning unit and a GRIN lens to produce a fast scanning focal spot offers a great potential to develop a compact endoscope probe for in vivo applications. To our best knowledge, our result is the first report on non-linear optical imaging of unstained rat oesophagus tissue with a miniaturized non-linear optical microscope based on a single fiber and a MEMS mirror. The technology will enable visualizations of functional and morphological changes of tissue at the microscopic level rather than direct observations with traditional instrument at the macroscopic level. Further integration of a 2-D MEMS mirror[25] and a large diameter GRIN lens will allow for real-time imaging with a field of view up to a hundred micrometers. We therefore expect the nonlinear optical endoscope to complement other endoscopic imaging and enable optical biopsy for early cancer detection.

Development of PCF-Coupler-Based Nonlinear Endoscopy

As mentioned above, in recent years, fiber-optic-based microscopy and endoscopy have enabled in vivo fluorescence imaging in live animals due to its mechanical flexibility and compact size. Important progress made in two-photon and second harmonic generation fiber-optic imaging is the adoption of double-clad photonic crystal fibers (PCFs) to improve the detection efficiency of the imaging system. Compared with conventional fibers, the double-clad PCF plays a dual role to deliver the excitation beam in the single-mode central core and collect emissions via the large-area inner cladding region with a high numerical aperture. In particular, the dual function offered by the double-clad PCF allows the miniaturization of the nonlinear microscope probe to be incorporated into a working channel of the endoscope by use of a single piece of fiber[35]. To achieve a further miniaturization of compact nonlinear optical microscopy, one can use a multiport PCF coupler to replace the dichroic mirror for an all-fiber imaging system[7]. At present basic devices fabricated by PCFs have not been commercially available[36,37], although a broad range of developments and applications of PCFs are revolutionizing fiber-optic design and performance. Here we report on the development of a nonlinear optical endoscope based on a custom-fabricated double-clad PCF coupler. Optical design and key technology foundations of such nonlinear optical endoscopy are discussed.

Optical Design

Figure 17:
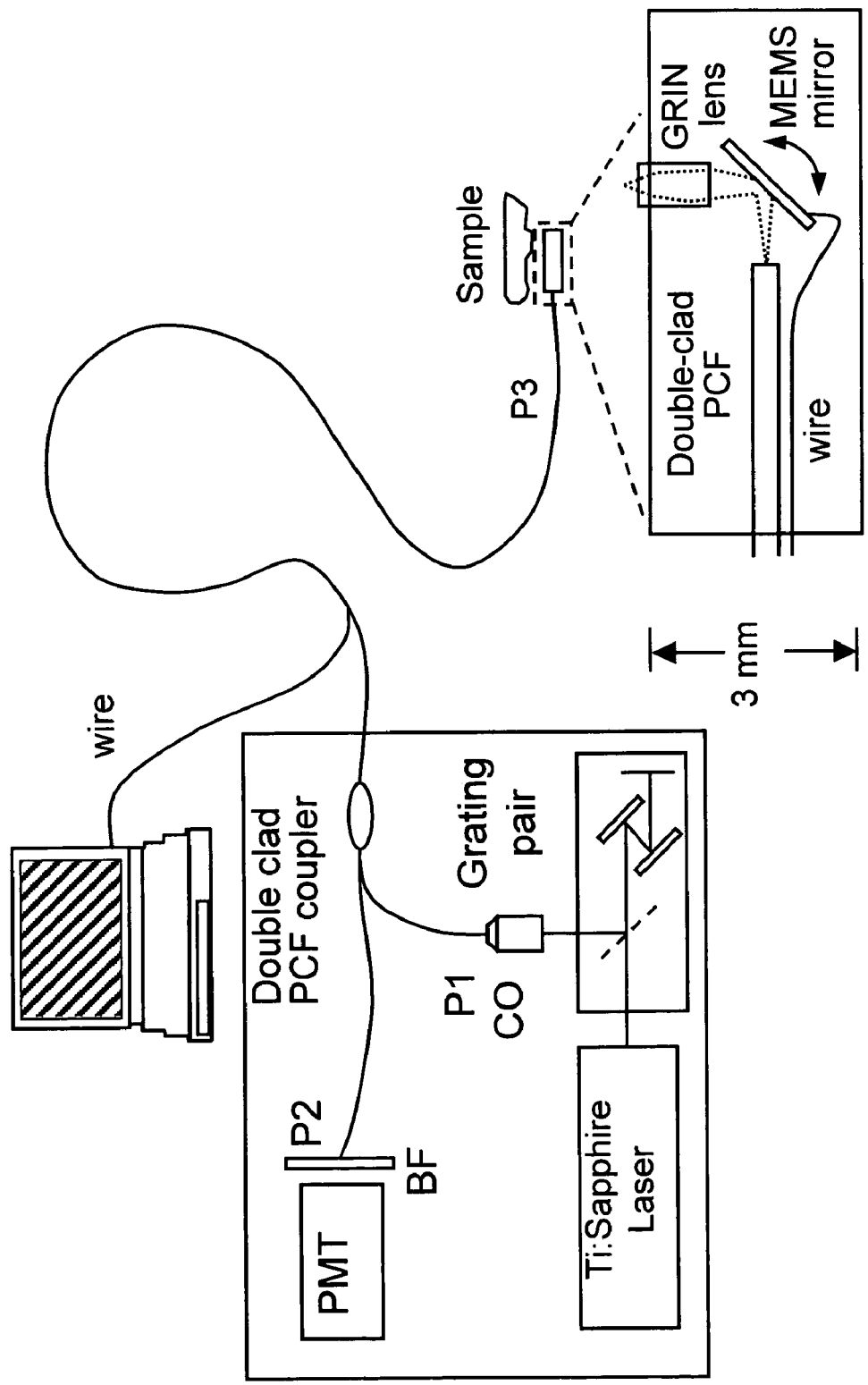
FIG. 17 illustrates a schematic diagram of a nonlinear optical endoscope based on a double-clad PCF coupler, a GRIN lens and a MEMS mirror. However, the MEMS mirror is not used in FIGS. 18-20.

FIG. 17 shows the design of a nonlinear optical endoscope consisting of a double-clad PCF coupler, a GRIN lens and a MEMS mirror. Ultrashort laser pulses are prechirped and delivered by one port of the double-clad PCF coupler. The MEMS mirror reflects and steers the excitation light on the back surface of GRIN lens which produces a diffraction-limited focus spot on the sample. Nonlinear signals from the sample are collected via a detection arm of the coupler into a photomultiplier tube. It should be pointed out that for the design of a flexible endoscope probe, the use of a single GRIN lens of short pitch is critical to reduce the size of probe and suppress optical aberration occurred in the GRIN medium.

Performance of the Double-Clad PCF Coupler

The double-clad PCF is used to make the coupler by the fused biconical tapered method (Fovice, Korea). To obtain optimum delivery of the pulsed laser beam and collection of nonlinear signals, we first measure the coupling efficiency and output mode profile at different ports in visible and NIR wavelength ranges. The coupling efficiency at port 1 of the PCF coupler is approximately 55% with a splitting ratio of 98/2 between ports 1 and 2 with an excitation wavelength of 800 nm. The output pattern from port 1 is consistent with FIG. 1(h) in reference 37, indicating the single-mode guidance of the pulsed laser beam in the central core. However, single-mode propagation from port 2 is not observed. The coupling efficiency from ports 3 to 2 is approximately 0.2%, illuminated by a CW beam of wavelength 532 nm. As a result, using port 1 for delivery of the pulsed laser beam and port 2 for signal collection means that the novel double-clad PCF coupler succeeds in possessing the unique property of double-clad PCF and that nonlinear signals can be optimized.

The effectiveness of the double-clad PCF coupler for nonlinear imaging is demonstrated by the three-dimensional two-photon fluorescence images of 10-μm-diameter microspheres, shown in FIG. 2. The series of microspheres images exhibit high contrast and the optical sectioning ability of the system. Compares with the two-photon fluorescence images obtained from the single-mode-fiber-coupler-based endoscope[23], the contrast enhancement in the PCF coupler-based endoscope might be due to the large illumination area (~17 μm) of a double-clad PCF.

Dispersion Management

Propagation of ultrashort pulses through an optical fiber results in significant temporal broadening of the pulses due to the group-velocity dispersion (GVD) and the self-phase modulation. The different frequency components of a pulse travel at slightly different speeds along the fiber because of GVD. Because red components of the pulse spectrum travel faster in the fused silica material of the fiber at 800 nm than blue components, the pulse leaving the fiber is lengthened and frequency modulated (positive chirped). It turns out that blue components occur near the trailing edge of the pulse whereas the leading edge consists of the red components. It is possible to compensate for GVD by negatively prechirping the pulse by giving different time delays initially for different frequency components during their passage through the grating pair. Thus the trailing edge catches up with the leading edge during the passage of the pulse through the fiber. When the amount of negative prechirp exactly compensates for that of the positive chirp caused by the fiber, the pulsewidth leaving the fiber will be minimized.

Figure 18:
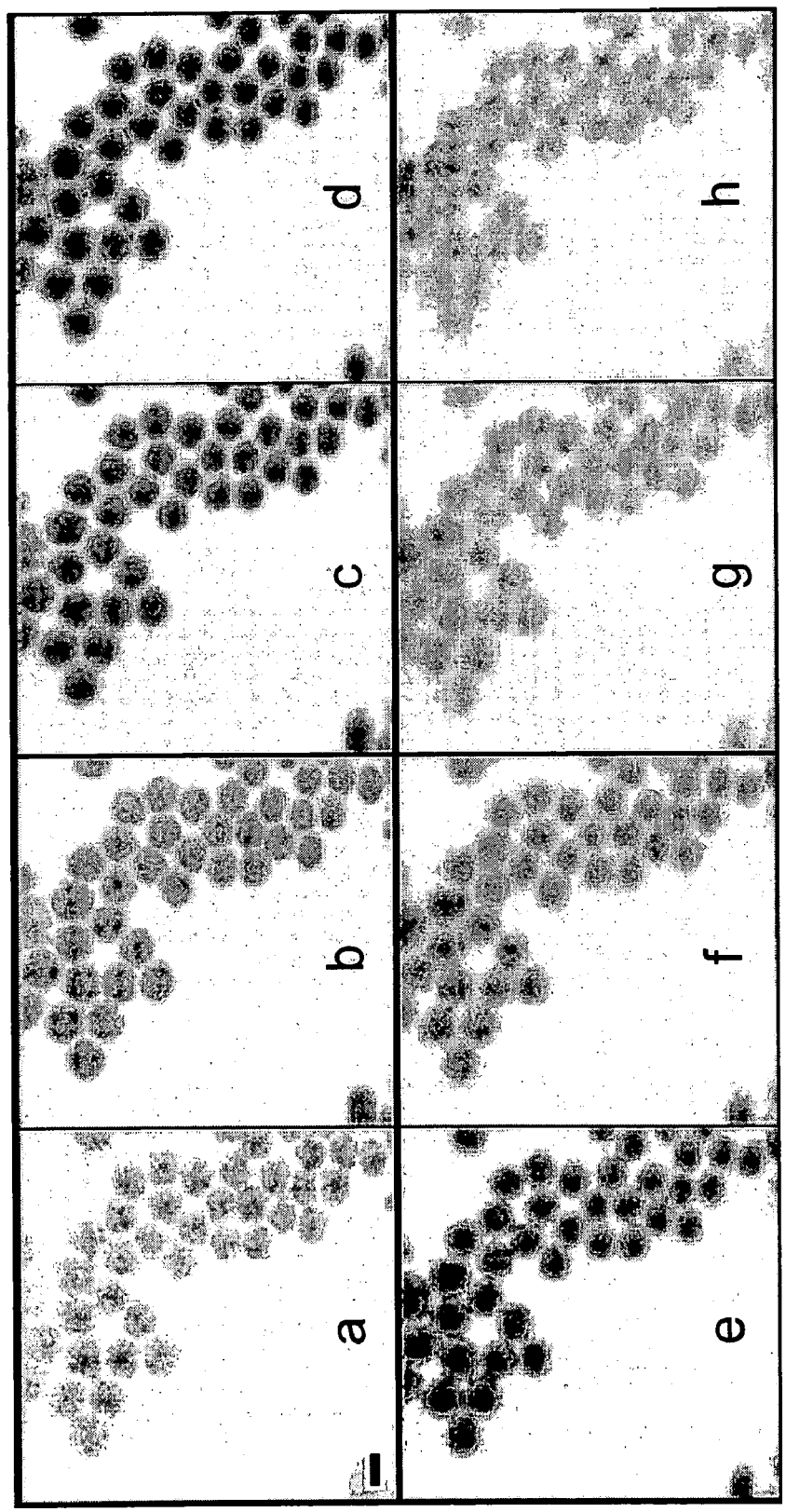
FIG. 18 shows negative images of 10-µm-diameter microspheres in a two-photon fluorescence endscope with a double-clad PCF coupler; the scale bar represents 10 µm and the slice spacing is 5 µm.
Figure 19:
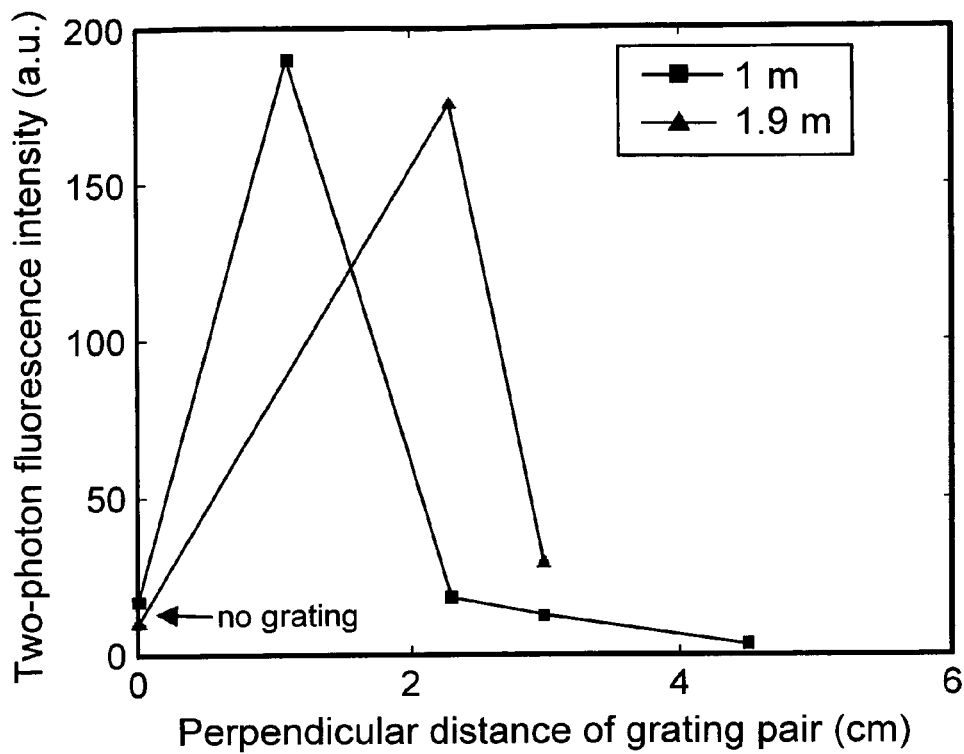
FIG. 19 illustrates detected two-photon fluorescence strength as a function of grating pair spacing for fiber lengths of 1 m and 1.9 m.

Here anomalous GVD is provided by double passing a diffraction grating pair (1200 grooves/mm, 28.7 blaze angle; Newport) to compress the pulse width. The grating pair provides anomalous GVD with an effective GVD parameter given by Reference[38]

$$\beta_2^{eff} = \frac{-8\pi^2 c}{\varpi_0^3 d^2 \cos^2\Theta} = \frac{-\lambda^3}{\pi c^2 d^2 \cos^2\Theta} \quad (3)$$

Where $\lambda$ is the illumination wavelength, d is the line spacing of the grating and $\Theta$ is the diffraction angle of incident light. A negative prechirp is required to compensate for fiber of proper length corresponding to a GVD parameter of 322 fs2/cm expected for silica. The variation of the detected two-photon fluorescence strength versus the perpendicular distance between the grating pair is depicted in the negative images of FIG. 18 for pulses propagating through a 1-m and a 1.9-m long double clad PCFs respectively. It can be seen that two-photon fluorescence intensity is maximized by setting the proper spacings between the grating pair to compensate the positive dispersion caused by the fibers.

Figure 20:
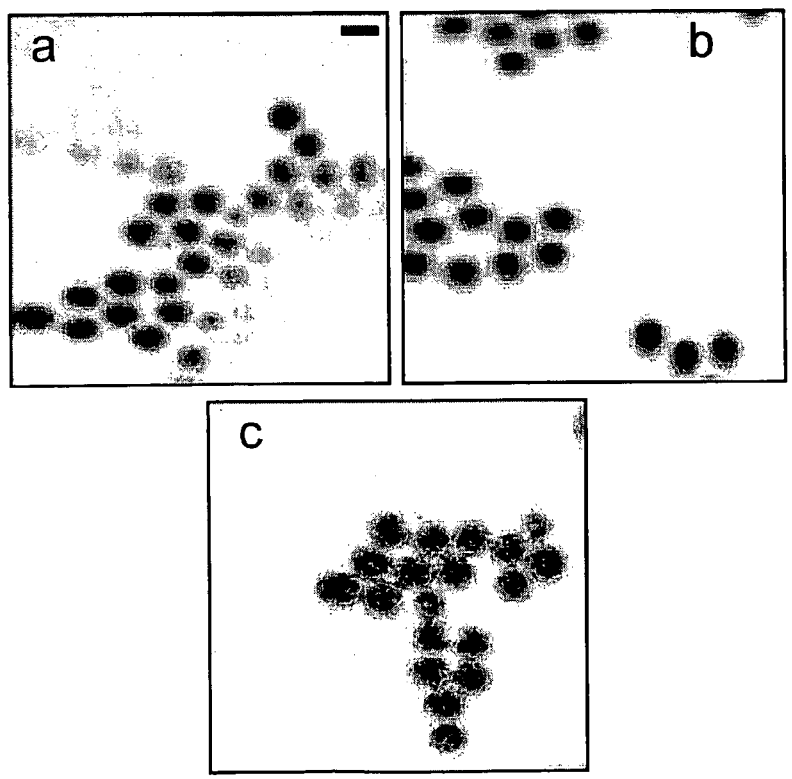
FIG. 20 shoes (a) two-photon fluorescence images obtained with a PCF-GRIN-based microscope with dispersion compensation. Applied voltage of PMT is 455V and excitation power is 0.6 mW; (b) a negative two-photon fluorescence image obtained with PCF-GRIN-based microscope. Applied voltage of PMT is 455V and excitation power is 2.3 mW; (c) a negative two-photon fluorescence image obtained with a single-mode-fiber coupler-GRIN-based coupler-GRIN-based microscope. Applied voltage of PMT is 703V and excitation power is 11 mW.

To demonstrate the effect of negative prechirp on nonlinear imaging systems, in FIGS. 20, (a) and (b) are negative two-photon fluorescence images of microspheres obtained from the PCF-GRIN-based nonlinear microscope with dispersion compensation and without dispersion compensation, respectively. It shows that the signal level is improved by a factor of approximately 12 times after grating pair is used to cancel the positive GVD in the PCF. Compared with the imaging performance of the nonlinear microscope based on a single-mode fiber-coupler and GRIN lens without pulse compression, the detected signal is three orders of magnitude higher by use of a double-clad PCF and a dispersion compensation unit. It is no doubt that this dispersion compensation method can be adopted to improve the signal level in the PCF-coupler-based system as well.

From the miniaturization point of view, another suitable method would be the inclusion of an in-fiber Bragg grating since this allows freedom of the fiber from bulk gratings. Additionally, two-dimensional microstructure in PCFs offer a wealth of opportunities to control properties of the fiber, such as the dispersion and the birefringence. For example, zero group velocity dispersion can be achieved by subtly engineering waveguide dispersion of photonic crystal structures and material dispersion of photonic crystal material. Such dispersion engineering enables spectacular nonlinear effects such as the generation of single-mode broadband optical supercontinuum, which will allow multi-channel multi-modality endoscopic imaging. And again, careful design of the photonic crystal structure in the fiber will make a fiber with a very large core size to carry more power than standard fibers. Birefringence PCF fibers also can be designed to preserve the polarization of second harmonic generated from structured protein[39,40]. These technology described above would provide new opportunities for photonic crystal fiber devices and have significant impact on its applications to nonlinear optical endoscopy.

Optimization of Splitting Ratio

Splitting ratio of a PCF coupler is the coupling ratio that couples light from one PCF to another PCF, playing an important role in the efficiency of excitation delivery and signal collection. Specifically, the nonlinear dependence of emitted signals on the excitation power in the nonlinear optical processes gives rise to a nonlinear dependence of the splitting ratio on the detected signals by the PCF coupler. Therefore, splitting ratio of the PCF coupler can be optimum designed to maximize the detected strength of nonlinear signals.

Figure 21A:
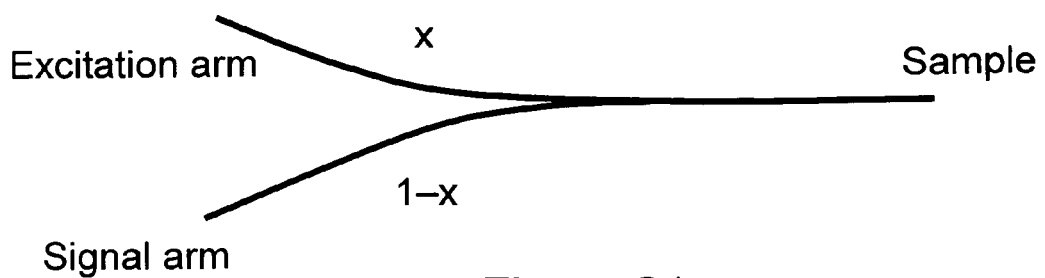
FIG. 21(a) is a schematic diagram of a three-port coupler with a splitting ratio of x/(1−x). Figures (b)-(c) illustrate detected nonlinear signal intensity as a function of coupling ratio to excitation arm in two and three-photon processes.
Figure 21B:
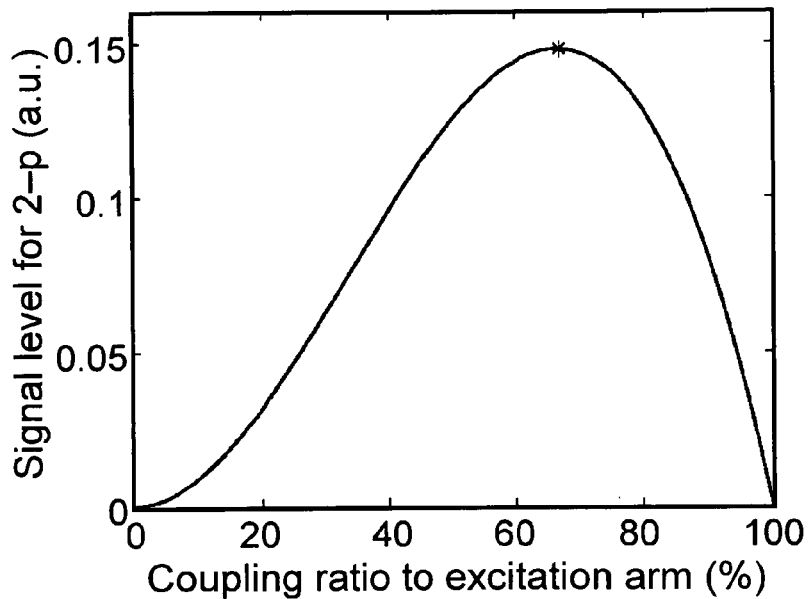
Figure 21C:
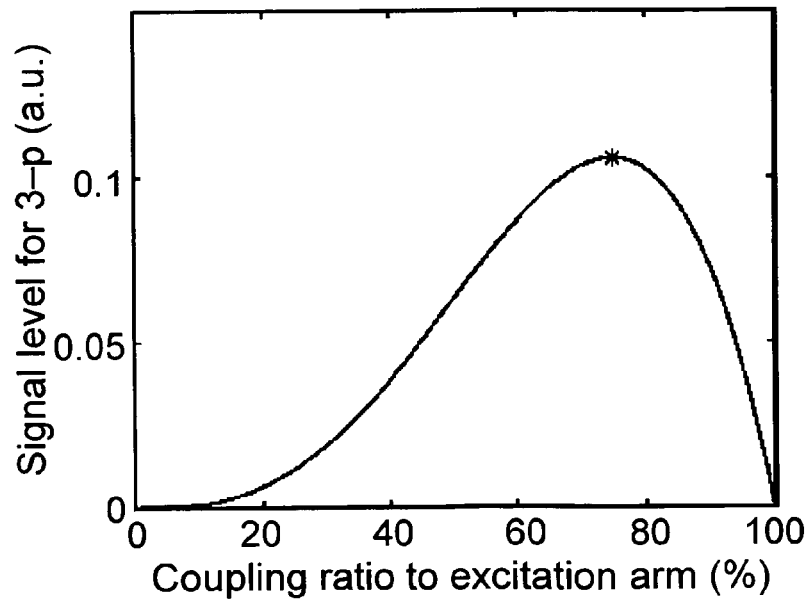

Let us consider a three-ports fiber coupler with a splitting ratio of $x/(1-x)$ if the loss is neglected, as shown in FIG. 21($a$). The coupling efficiency between two ports of the coupler is linearly dependent on the coupling ratio $x$ and $(1-x)$. For an n-photon excitation process, if the splitting ratio is consistent at excitation and emission wavelength, the detected fluorescence intensity is given by $$I_f \propto I_i^n x^n (1-x) \quad (4)$$

FIG. 21($b$) depicts the detected nonlinear signal intensity as a function of the coupling ratio to the excitation arm in the case of two-photon or second harmonic generation process. It can be observed that the optimized splitting ratio between an excitation arm and a signal arm is 67/33. In the case of three-photon or third harmonic generation process, the optimized splitting ratio between an excitation arm and a signal arm is 75/25. Indeed, the optical fiber coupler that will be integrated to a nonlinear imaging or sensor system could be fabricated to maximize detection efficiency based on the above estimations.

Scanning Mechanism

A two-dimensional MEMS mirror that relies on electrostatic actuation will be suitable for the nonlinear imaging system due to low consumption, the millimeter size, and the compatibility with optics. In particular, a 1-mm-size MEMS has mechanical resonance frequency of hundreds of Hz, enabling video-rate imaging acquisition with large scanning angle (>30°). Therefore, inclusion of a two-dimensional MEMS mirror in the nonlinear optical endoscope will allow for real-time imaging in endoscopic applications.

Toward Applications of Nonlinear Optical Endoscopy

Accordingly, to achieve an intact endoscopic image rather than a line profile through the nonlinear optical endoscope, a two-dimensional (2-D) scanning MEMS mirror should be incorporated into the endoscope probe.

Figure 22:
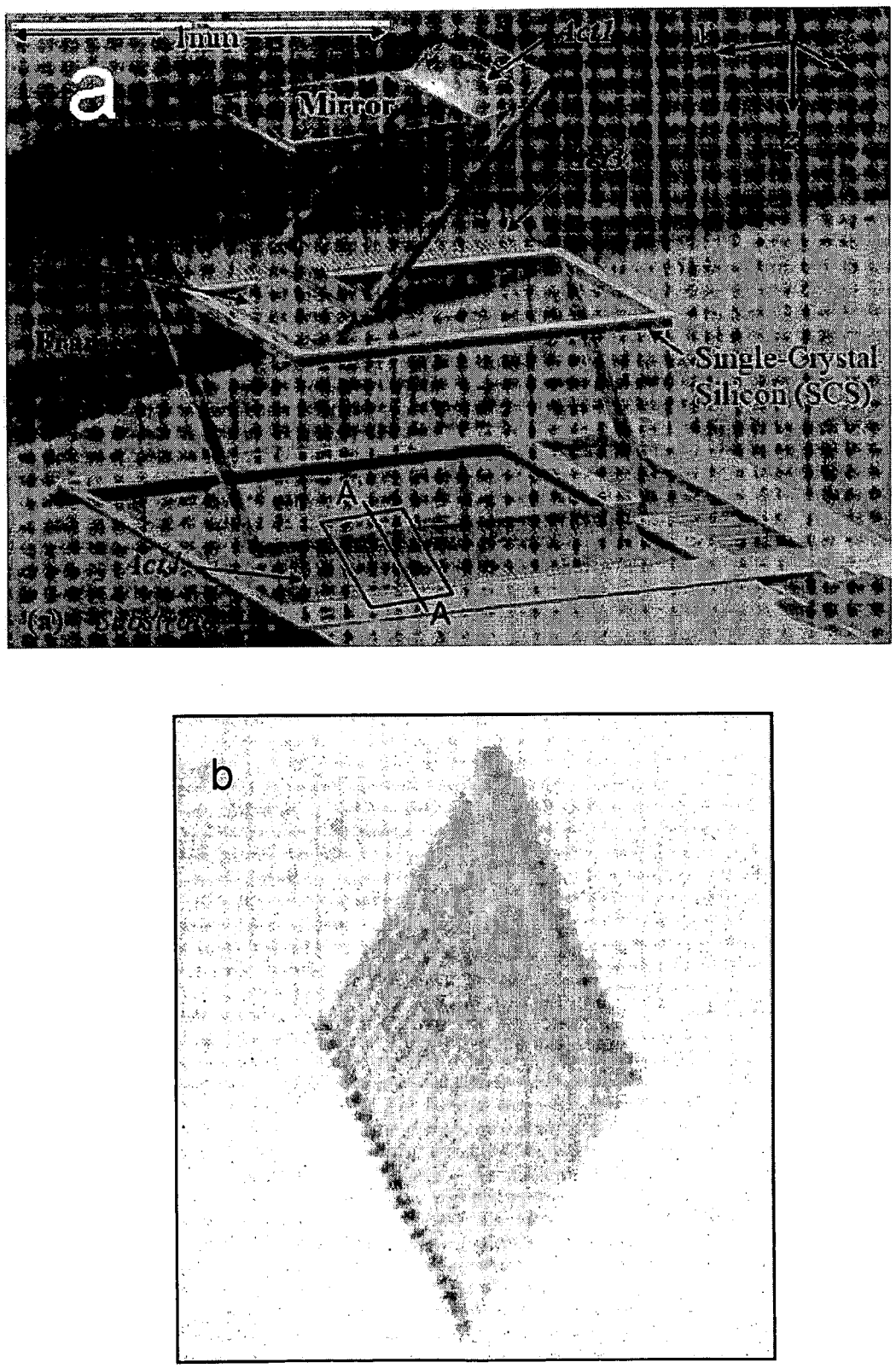
FIG. 22 illustrates (a) a scanning electron microscopy image of a 2D MEMS mirror and (b) a raster scanning pattern of the MEMS mirror.

The design of the new nonlinear optical endoscope is similar to that discussed previously, except for a modification to the excitation and detection paths to deliver higher excitation power to the sample. The 2-D micromirror (FIG. 22$a$) is based on electrothermal actuation to achieve a large optical scanning angle up to 35° at a low driving voltage of 10 V. A raster scanning (FIG. 22$b$) is created by driving two actuators of the micromirror with specially designed waveforms. Images are reconstructed according to the scanning calibration data.

The imaging capability of the nonlinear optical endoscope is demonstrated by the negative two-photon fluorescence imaging image (FIG. 23$a$) with 10 μm diameter fluorescent microspheres. It show that the 2-D MEMS mirror enables the efficient delivery of the light beam over broadband wavelength range and the smooth response for image acquisition. The performance of the system is also confirmed by the comparison between this image and the negative two-photon fluorescence image (FIG. 23$b$) obtained from a system based on a single-mode fibre coupler, a GRIN lens and a bulk scanning stage. It also should be pointed out that the single level of the nonlinear optical endoscope is approximately 120 times higher than the microscope system using a single-mode fibre coupler and a bulk scanning mechanism.

Figure 25:
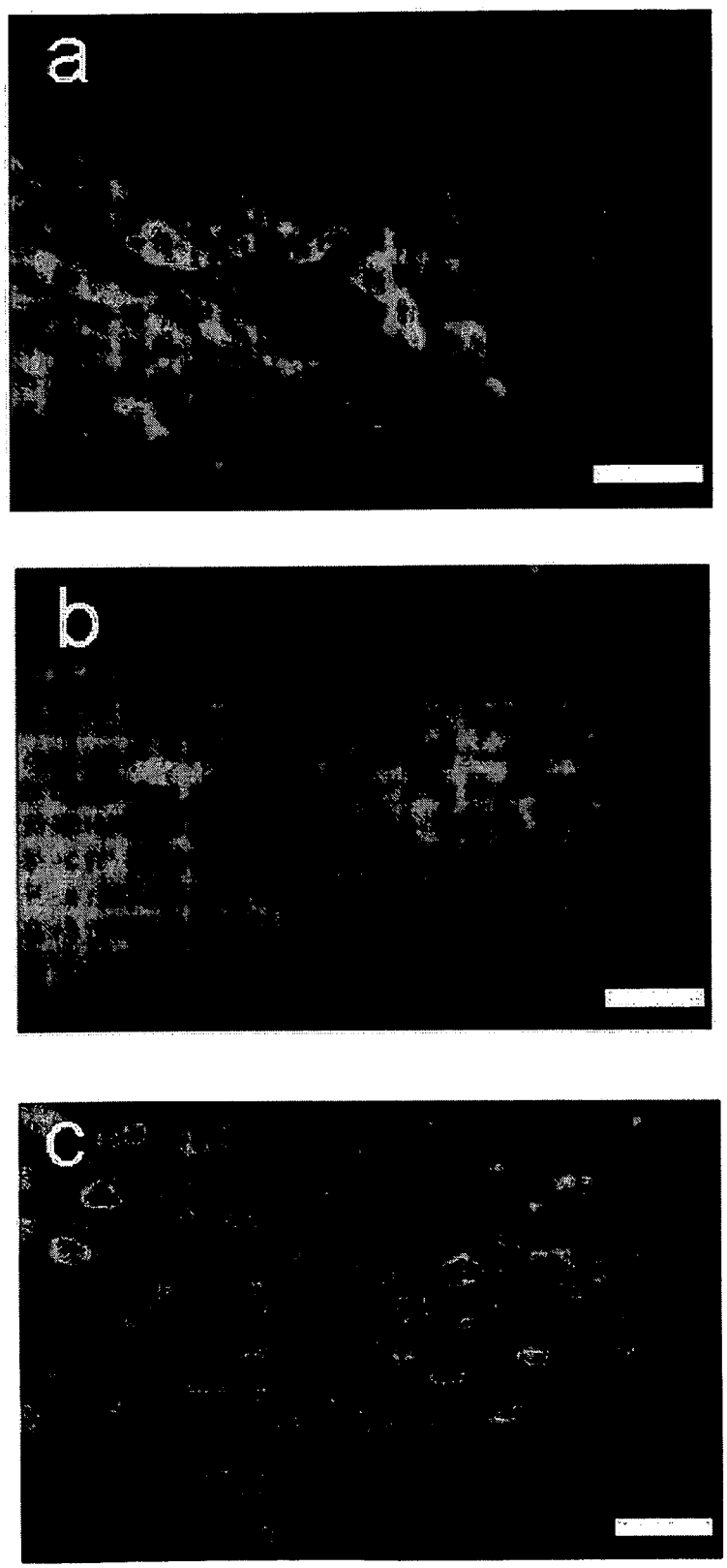
FIG. 25 shows (a) porcine buccal cavity mucosal tissue topically stained with acridine orange (1% in Hank's Balanced Salt Solution. Stained stratified squamous epithelial cell nuclei can be seen over the underlying lamina propria region. (b) Porcine oropharynx tissue topically stained with acridine orange (1% in Hanks Balanced Salt Solution). Stained epithelial cell nuclei can be seen. (c) Porcine inner lip endothelial tissue. Surface squamal cells can be clearly identified over the underlying lamina propria region. All scale bars represent 20 µm.

There are a number of promising clinical applications for the nonlinear optical endoscope. One such application is in imaging a gastrointestinal tract and oral cavity. FIG. 24 shows in vitro images of excised rat colon and stomach tissues. Although there are endogenous fluorescence and harmonic contrasts in most tissues, a nucleic acid stain such as acridine orange is used to enhance the imaging contrast significantly. FIG. 25 shows in vitro images of three different parts in a pig head. Again, the porcine tissues are stained with acridine orange. The observation of the epithelial surface is straightforward. Future investigations will be related to greater functionality and cancer detection.

In conclusion, we have presented the design of a compact system including a double-clad PCF coupler, a GRIN lens and a MEMS mirror, which will lead to the next generation of nonlinear optical endoscopy. Feasibility of the laboratory-built double-clad PCF coupler for nonlinear imaging has been demonstrated by two-photon fluorescence images of microspheres. Further improvement of the signal level of the nonlinear endoscope system would be achieved by the dispersion compensation and optimization of the splitting ratio of the PCF coupler. Together, advances of those rapidly emerged techniques will propel the developments and applications of nonlinear optical endoscopy.

The invention has been described, by way of non-limiting example only and many modifications and variations may be made thereto without departing from the spirit and scope of the invention described.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

REFERENCES

1. W. R. Zipfel, R. M. Williams and W. W. Webb, "Nonlinear magic: multiphoton microscopy in the biosciences", Nat. Biotech. 21, 1369 (2003).
2. P. J. Campagnola and L. M. Loew, "Second harmonic imaging microscopy for visualizing biomolecular arrays in cells, tissues and organisms", Nat. Biotech. 21, 1356 (2003).
3. J. C. Jung and M. J. Schnitzer, "Multiphoton endoscopy", Opt. Lett. 28, 902 (2003).
4. D. Bird and M. Gu, "Compact two-photon fluorescence microscope based on a single-mode fiber coupler", Opt. Lett. 27, 1031 (2002).
5. D. Bird and M. Gu, "Resolution improvement in two-photon fluorescence microscopy with a single-mode fiber", Appl. Opt. 41, 1852 (2002).
6. D. Bird and M. Gu, "Fibre-optic two-photon scanning fluorescence microscopy", J. Micros. 208, 35 (2002).
7. D. Bird and M. Gu, "Two-photon fluorescence endoscopy with a micro-optic scanning head", Opt. Lett. 28, 1552 (2003).
8. L. Fu, X. Gan, and M. Gu, "Use of a single-mode fiber coupler for second-harmonic-generation microscopy", Opt. Lett. 30, 385 (2005).
9. W. Göbel, J. N. D. Kerr, A. Nimmerjahn, and F. Helmchen, "Miniaturized two-photon microscope based on a flexible coherent fiber bundle and a gradient-index lens objective," Opt. Lett. 29, 2521-2523 (2004).
10. J. Limpert, T. Schreiber, S. Nolte, H. Zellmer, A. Tunnermann, R. Iliew, F. Lederer, J. Broeng, G. Vienne, A. Petersson, and C. Jakobsen, "High-power air-clad large-mode-area photonic crystal fiber laser", Optics Express 11, 818 (2003).
11. M. T. Myaing, J. Y. Ye, T. B. Norris, T. Thomas, J. R. Baker, W. J. Wadsworth, G. Bouwmans, J. C. Knight, and P. St. J. Russell, "Enhanced two-photon biosensing with double-clad photonic crystal fibers", Opt. Lett. 28, 1224 (2003).
12. D. Yelin, B. E. Bouma, S. H. Yun, and G. J. Teamey, "Double-clad fiber for endoscopy", Opt. Lett. 29, 2408 (2004).
13. A. Bjarklev, J. Broeng, A. S. Bjarklev, Photonic Crystal Fibers (Kluwer Academic Publishers, Norwell, Boston, 2003).
14. E. B. Brown, R. B. Campbell, Y. Tsuzuki, L. Xu, P. Carmeliet, D. Fukumura, and R. K. Jain, "In vivo measurement of gene expression, angiogenesis and physiological function in tumors using multiphoton laser scanning microscopy," Nat. Med, 7, 864-868 (2001).
15. C Stosiek, O. Garaschuk, K. Holthoff, and A. Konnerth. "In vivo two-photon calcium imaging of neuronal networks," Proc. Natl. Acad. Sci. 100, 7319-7324 (2003).
16. W. Denk, J. H. Strickler, and W. W. Webb, "Two-photon laser scanning fluorescence microscopy," Science. 248, 73-75 (1990).
17. J. Knittel, L. Schnieder, G. Buess, B. Messerschmidt, and T. Possner, "Endoscope-compatible confocal microscope using a gradient index-lens system," Opt. Commun. 188, 267-273 (2001).
18. B. E. A. Saleh and M. C. Teich, *Fundamentals of Photonics* (John Wiley, New York, 1991).
19. M Gu, *Principles of Three-Dimensional Imaging in Confocal Microscopes* (World Scientific, Singapore, 1996).
20. M. Gu and C. J. R. Sheppard, "Signal level of the fiber-optical confocal scanning microscope," J. Mod. Opt. 38, 1621-1630 (1991).
21. M. Gu and D. Bird, "Three-dimensional optical transfer-function analysis of fiber-optical two-photon fluorescence microscopy," J. Opt. Soc. Am. A 20, 941-947 (2003).
22. L. Fu, X. Gan, and M. Gu, "Characterization of the GRIN lens-fiber spacing toward applications in two-photon fluorescence endoscopy," Applied Optics 44, 7270-7274 (2005).
23. W. E. Zipfel, R. M. Williams, R. Christie, A. Y. Nikitin, B. T. Hyman, and W. W. Webb, "Live tissue intrinsic emission microscopy using multiphoton-excited native fluorescence and second harmonic generation," PNAS 100, 7075 (2003).
24. A. Jain, A. Kopa, Y. Pan, G. K. Fedder, H. Xie, "A two-axis electrothermal micromirror for endoscopic optical coherence tomography," Quantum electronics 10, 636 (2004).
25. Helmchen, F., Fee, M. S., Tank, D. W. & Denk, W. A miniature head-mounted two-photon microscope: High-resolution brain imaging in freely moving animals. Neuron 31, 903-912 (2001).
26. Bird, D. & Gu, M. Compact two-photon fluorescence microscope based on a single-mode fiber coupler. *Opt. Lett.* 27, 1031-1033 (2002).
27. Jung, J. C., Mehta, A. D., Aksay, E., Stepnoski, R. & Schnitzer, M. J. In vivo mammalian brain imaging using oneand two-photon fluorescence microendoscopy. *J. Neurophysiol.* 92, 3121-3133 (2004).
28. Levene, M. J., Dombeck, D. A., Kasischke, K. A., Molloy, R. P. & Webb, W. W. In vivo multiphoton microscopy of deep brain tissue. *J. Neurophysiol.* 91, 1908-1912 (2004).
29. Kim, D., Kim, K. H., Yazdanfar, S. & So, P.T.C. in Multiphoton Microscopy in the Biomedical Sciences V (eds. Periasamy, A. & So, P. T. C.) (Preceeding of SPIE, Bellingham, Wash., 2005).
30. Flusberg, B. A., Jung, J. C., Cocker, E. D., Anderson, E. P. & Schnitzer, M. J. In vivo brain imaging using a portable 3.9 gram two-photon fluorescence microendoscope. *Opt. Lett.* 30, 2272-2274 (2005).
31. Ye, J. Y. in Multiphoton Microscopy in the Biomedical Sciences V (eds. Periasamy, A. & So, P. T. C.) (Preceeding of SPIE, Bellingham, Wash., 2005).
32. Fu, L., Gan, X. & Gu, M. Nonlinear optical microscopy based on double-clad photonic crystal fibers. *Opt. Express* 13, 5528-5534 (2005).
33. Xie, H., Pan, Y. & Fedder, G. K. Endoscopic optical coherence tomographic imaging with a CMOS-MEMS micromirror. *Sensors and Actuators* 103, 237-241 (2003).
34. George, M. Optical methods and sensors for in situ histology in surgery and endoscopy. *Min. Invas. Ther. & Allied. Technol.* 13, 95-104 (2004).
35. L. Fu, A. Jain, H. Xie, C. Cranfield and M. Gu, "Nonlinear optical endoscopy based on a double-clad photonic crystal fiber and a MEMS mirror.", Optics Express 14, 1027-1032 (2006).
36. Lee, B. H., Eom, J. B., Kim, J., Moon, D. S., and Paek, U. Photonic crystal fiber coupler. Opt. Lett. 27, 812-814 (2002).
37. Kim, H., Kim, J., Paek, U., and Lee, B. Tunable photonic crystal fiber coupler based on a side-polishing technique. Opt. Lett. 29, 1194-1196 (2004).
38. Agrawal, G. P. *Nonlinear fiber optics*. Academic Press (1989).
39. Knight, J. C. and Russell, P. St. J. New ways to guide light. *Science* 296, 276-277 (2002).

40. Knight, J. C. Photonic crystal fibers. *Nature* 424, 847-851 (2003).

The claims defining the invention are as follows:

1. A fiber coupler, comprising:
    a first optical fiber and a second optical fiber, each of said fibers comprising a single-mode core and a multi-mode layer surrounding said core, said respective multi-mode layers having a numerical aperture greater than a numerical aperture of said respective cores and a compensator for compensating for signal dispersion resulting from group-velocity dispersion and comprising a grating structure;
    wherein said multi-mode layer of said first fiber is fused to said multi-mode layer of said second optical fiber, and said cores of said first and second fibers are configured not to couple light from said core of said first fiber into said core of said second fiber.

2. A coupler as claimed in claim 1, wherein said first optical fiber and said second optical fiber comprise photonic crystal fibers.

3. An imaging system, comprising: a fiber coupler comprising a first optical fiber and a second optical fiber, each of said fibers comprising a single-mode core and a multi-mode layer surrounding said core, said respective multi-mode layers having a numerical aperture greater than a numerical aperture of said respective cores, wherein said multi-mode layer of said first fiber is fused to said multi-mode layer of said second optical fiber, and said cores of said first and second fibers are configured not to couple light from said core of said first fiber into said core of said second fiber; and a compensator for compensating for signal dispersion resulting from group-velocity dispersion and comprising a grating structure.

4. An imaging system as claimed in claim 3, wherein said system forms part of an endoscope.

5. An imaging system as claimed in claim 3, including a gradient index (GRIN) lens.

6. An imaging system as claimed in claim 5, including a multi-mode fiber.

7. An imaging system as claimed in claim 6, wherein the GRIN lens is positioned in spaced relation relative to an end of said fiber.

8. An imaging system as claimed in claim 6, wherein the lens has a pitch of between 0.2 and 0.29 and is spaced from the fiber by a distance of between 0.5 and 10 mm.

9. An imaging system as claimed in claim 3, including a scanning mechanism comprising a microelectromechanical system (MEMS) mirror, for reflecting an excitation signal in varying directions in order to scan a sample.

10. An imaging system as claimed in claim 3, wherein said compensator comprises a grating pair or Bragg grating.

11. An imaging system as claimed in claim 3, wherein said compensator is configured to provide prechirping.

12. An imaging system as claimed in claim 3, wherein said coupler has a splitting ratio optimised to enhance detection efficiency of said system.

13. A method of splitting an optical signal, comprising:
    transmitting said signal into a first optical fiber of a fiber coupler comprising said first optical fiber and a second optical fiber, each of said fibers comprising a single-mode core and a multi-mode layer surrounding said core, said respective multi-mode layer having a numerical aperture greater than a numerical aperture of said respective core, wherein said first multi-mode layer is fused to said second multi-mode layer, and said first cores is not fused to said second core;
    coupling a first component of said signal transmitted in said multi-mode layer of said first optical fiber into said multi-mode layer of said second optical fiber; and
    minimizing coupling of a second component of said signal transmitted in said core of said first optical fiber into said core of said second optical fiber; and compensating for signal dispersion resulting from group-velocity dispersion with a compensator comprising a grating structure.

14. A method as claimed in claim 13, wherein said first optical fiber and said second optical fiber comprise photonic crystal fibers.

15. A fiber coupler, comprising:
    a first optical fiber and a second optical fiber, each of said fibers comprising a single-mode core and a multi-mode layer surrounding said core, said respective multi-mode layers having a numerical aperture greater than a numerical aperture of said respective cores; and
    a compensator for compensating for signal dispersion resulting from group-velocity dispersion;
    wherein said multi-mode layer of said first fiber is fused to said multi-mode layer of said second optical fiber, and said cores of said first and second fibers are configured not to couple light from said core of said first fiber into said core of said second fiber.

16. An imaging system as claimed in claim 15, wherein said compensator is configured to provide prechirping.

17. A method of splitting an optical signal, comprising:
    transmitting said signal into a first optical fiber of a fiber coupler comprising said first optical fiber and a second optical fiber, each of said fibers comprising a single-mode core and a multi-mode layer surrounding said core, said respective multi-mode layer having a numerical aperture greater than a numerical aperture of said respective core, wherein said first multi-mode layer is fused to said second multi-mode layer, and said first cores is not fused to said second core;
    coupling a first component of said signal transmitted in said multi-mode layer of said first optical fiber into said multi-mode layer of said second optical fiber;
    minimizing coupling of a second component of said signal transmitted in said core of said first optical fiber into said core of said second optical fiber; and
    compensating for signal dispersion resulting from group-velocity dispersion.

* * * * *